US008333985B2

(12) United States Patent  (10) Patent No.: US 8,333,985 B2
Knaack et al.  (45) Date of Patent: Dec. 18, 2012

(54) NON-GLYCEROL STABILIZED BONE GRAFT

(75) Inventors: David Knaack, Summit, NJ (US); Michele Diegmann, Scotch Plains, NJ (US); Albert Manrique, Manalapan, NJ (US); Keyvan Benham, Red Bank, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1476 days.

(21) Appl. No.: 10/589,226

(22) PCT Filed: Jan. 27, 2005

(86) PCT No.: PCT/US2005/003092
§ 371 (c)(1), (2), (4) Date: Dec. 20, 2006

(87) PCT Pub. No.: WO2005/072656
PCT Pub. Date: Aug. 11, 2005

(65) Prior Publication Data
US 2007/0178158 A1  Aug. 2, 2007

Related U.S. Application Data

(60) Provisional application No. 60/539,555, filed on Jan. 27, 2004.

(51) Int. Cl.
*A61F 2/28* (2006.01)
(52) U.S. Cl. ..................................................... 424/425
(58) Field of Classification Search .................. None
See application file for complete search history.

(56) References Cited

U.S. PATENT DOCUMENTS

| | | | |
|---|---|---|---|
| 1,025,008 | A | 4/1912 | Miner |
| 2,375,116 | A | 5/1945 | Larkin |
| 2,525,222 | A | 10/1950 | Holt |
| 3,068,916 | A | 12/1962 | Richardson |
| 3,486,505 | A | 12/1969 | Morrison |
| 3,604,298 | A | 9/1971 | Dekiel |
| 3,604,487 | A | 9/1971 | Gilbert |
| 3,703,006 | A | 11/1972 | Sharma |
| 3,848,601 | A | 11/1974 | Ma et al. |
| 4,033,244 | A | 7/1977 | Jacobson |
| 4,059,115 | A | 11/1977 | Jumashev et al. |
| 4,185,383 | A | 1/1980 | Heimke et al. |

(Continued)

FOREIGN PATENT DOCUMENTS

AU  744371  11/1998

(Continued)

OTHER PUBLICATIONS

Albee, Fred H., "Bone Surgery with Machine Tools," *Scientific American*, Apr. 1936, pp. 178-181.

(Continued)

*Primary Examiner* — Carlos Azpuru

(57) ABSTRACT

A demineralized bone matrix (DBM) or other matrix composition is provided that has been stabilized by lowering the pH of the composition, reducing the water content, adding water substitutes, and/or increasing the amount of deuterated water present in the composition in order to reduce the activity of endogenous degrading enzymes such as proteases. A hydrated form of a stabilized DBM composition may be stable up to a year at room temperature at acidic pH. The acidified DBM compositions may be further stabilized by the addition of a stabilizing agent such as deuterated water, water substitutes, polymers, protease inhibitors, glycerol or hydrogels.

25 Claims, 3 Drawing Sheets

U.S. PATENT DOCUMENTS

| | | |
|---|---|---|
| 4,273,117 A | 6/1981 | Neuhauser |
| 4,349,921 A | 9/1982 | Kuntz |
| 4,394,370 A | 7/1983 | Jefferies |
| 4,416,278 A | 11/1983 | Miller |
| 4,440,750 A | 4/1984 | Glowacki et al. |
| 4,484,570 A | 11/1984 | Sutter et al. |
| 4,485,097 A | 11/1984 | Bell |
| 4,516,276 A | 5/1985 | Mittelmeier et al. |
| 4,553,575 A | 11/1985 | Brown |
| 4,559,936 A | 12/1985 | Hill |
| 4,566,466 A | 1/1986 | Ripple et al. |
| 4,573,448 A | 3/1986 | Kambin |
| 4,637,931 A | 1/1987 | Schmitz |
| 4,649,918 A | 3/1987 | Pegg et al. |
| 4,678,470 A | 7/1987 | Nashef et al. |
| 4,714,469 A | 12/1987 | Kenna |
| 4,743,256 A | 5/1988 | Brantigan |
| 4,743,259 A | 5/1988 | Bolander et al. |
| 4,753,235 A | 6/1988 | Hasson |
| 4,772,287 A | 9/1988 | Ray et al. |
| 4,782,833 A | 11/1988 | Einhorn |
| 4,798,213 A | 1/1989 | Doppelt |
| 4,820,305 A | 4/1989 | Harms et al. |
| 4,834,757 A | 5/1989 | Brantigan |
| 4,863,477 A | 9/1989 | Monson |
| 4,877,020 A | 10/1989 | Vich |
| 4,878,915 A | 11/1989 | Brantigan |
| 4,904,261 A | 2/1990 | Dove et al. |
| 4,917,704 A | 4/1990 | Frey et al. |
| 4,932,973 A | 6/1990 | Gendler |
| 4,938,768 A | 7/1990 | Wu |
| 4,950,296 A | 8/1990 | McIntyre |
| 4,955,885 A | 9/1990 | Meyers |
| 4,961,740 A | 10/1990 | Ray et al. |
| 4,963,154 A | 10/1990 | Anapliotis et al. |
| 4,997,434 A | 3/1991 | Seedhom et al. |
| 5,015,255 A | 5/1991 | Kuslich |
| 5,026,373 A | 6/1991 | Ray et al. |
| 5,047,058 A | 9/1991 | Roberts et al. |
| 5,049,150 A | 9/1991 | Cozad |
| 5,053,049 A | 10/1991 | Campbell |
| 5,055,104 A | 10/1991 | Ray |
| 5,061,786 A | 10/1991 | Burnier et al. |
| 5,062,845 A | 11/1991 | Kuslich et al. |
| 5,112,354 A | 5/1992 | Sires |
| 5,171,278 A | 12/1992 | Pisharodi |
| 5,192,321 A | 3/1993 | Strokon |
| 5,192,327 A | 3/1993 | Brantigan |
| 5,197,967 A | 3/1993 | Wilson |
| 5,207,710 A | 5/1993 | Chu et al. |
| 5,236,456 A | 8/1993 | O'Leary et al. |
| 5,284,655 A | 2/1994 | Bogdansky et al. |
| 5,298,254 A | 3/1994 | Prewett et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,312,408 A | 5/1994 | Brown |
| 5,314,476 A | 5/1994 | Prewett et al. |
| 5,314,478 A | 5/1994 | Oka et al. |
| 5,361,483 A | 11/1994 | Rainville et al. |
| 5,380,333 A | 1/1995 | Meloul et al. |
| 5,390,683 A | 2/1995 | Pisharodi |
| 5,397,364 A | 3/1995 | Kozak et al. |
| 5,423,817 A | 6/1995 | Lin |
| 5,423,825 A | 6/1995 | Levine |
| 5,425,772 A | 6/1995 | Brantigan |
| 5,425,773 A | 6/1995 | Boyd et al. |
| 5,439,684 A | 8/1995 | Prewett et al. |
| 5,443,514 A | 8/1995 | Steffee |
| 5,445,639 A | 8/1995 | Kuslich et al. |
| 5,458,638 A | 10/1995 | Kuslich et al. |
| 5,458,643 A | 10/1995 | Oka et al. |
| 5,484,437 A | 1/1996 | Michelson |
| 5,489,307 A | 2/1996 | Kuslich et al. |
| 5,489,308 A | 2/1996 | Kuslich et al. |
| 5,490,962 A | 2/1996 | Cima et al. |
| 5,505,731 A | 4/1996 | Tornier |
| 5,505,732 A | 4/1996 | Michelson |
| 5,507,813 A | 4/1996 | Dowd et al. |
| 5,514,180 A | 5/1996 | Heggeness et al. |
| 5,518,680 A | 5/1996 | Cima et al. |
| 5,522,899 A | 6/1996 | Michelson |
| 5,534,028 A | 7/1996 | Bao et al. |
| 5,534,030 A | 7/1996 | Navarro et al. |
| 5,545,222 A | 8/1996 | Bonutti |
| 5,554,191 A | 9/1996 | Lahille et al. |
| 5,562,738 A | 10/1996 | Boyd et al. |
| 5,571,190 A | 11/1996 | Ulrich et al. |
| 5,571,192 A | 11/1996 | Schonhoffer |
| 5,591,235 A | 1/1997 | Kuslich |
| 5,593,409 A | 1/1997 | Michelson |
| 5,607,269 A | 3/1997 | Dowd et al. |
| 5,607,424 A | 3/1997 | Tropiano |
| 5,609,635 A | 3/1997 | Michelson |
| 5,609,636 A | 3/1997 | Kohrs et al. |
| 5,632,747 A | 5/1997 | Scarborough et al. |
| 5,645,596 A | 7/1997 | Kim et al. |
| 5,645,598 A | 7/1997 | Brosnahan, III |
| 5,653,761 A | 8/1997 | Pisharodi |
| 5,653,762 A | 8/1997 | Pisharodi et al. |
| 5,653,763 A | 8/1997 | Errico et al. |
| 5,658,336 A | 8/1997 | Pisharodi |
| 5,658,337 A | 8/1997 | Kohrs et al. |
| 5,662,710 A | 9/1997 | Bonutti |
| 5,669,909 A | 9/1997 | Zdeblick et al. |
| 5,683,394 A | 11/1997 | Rinner |
| 5,683,463 A | 11/1997 | Godefroy et al. |
| 5,683,464 A | 11/1997 | Wagner et al. |
| 5,702,391 A | 12/1997 | Lin |
| 5,707,371 A | 1/1998 | Metz-Stavenhagen |
| 5,709,683 A | 1/1998 | Bagby |
| 5,716,415 A | 2/1998 | Steffee |
| 5,716,416 A | 2/1998 | Lin |
| 5,720,751 A | 2/1998 | Jackson |
| 5,728,159 A | 3/1998 | Stroever et al. |
| 5,741,253 A | 4/1998 | Michelson |
| 5,749,916 A | 5/1998 | Richelsoph |
| 5,766,251 A | 6/1998 | Koshino |
| 5,766,252 A | 6/1998 | Henry et al. |
| 5,769,897 A | 6/1998 | Harle |
| 5,776,199 A | 7/1998 | Michelson |
| 5,782,830 A | 7/1998 | Farris |
| 5,782,919 A | 7/1998 | Zdeblick et al. |
| 5,785,710 A | 7/1998 | Michelson |
| 5,800,547 A | 9/1998 | Schafer et al. |
| 5,807,437 A | 9/1998 | Sachs et al. |
| 5,814,084 A | 9/1998 | Grivas et al. |
| 5,824,078 A | 10/1998 | Nelson et al. |
| 5,824,094 A | 10/1998 | Serhan et al. |
| 5,846,484 A | 12/1998 | Scarborough et al. |
| 5,860,973 A | 1/1999 | Michelson |
| 5,865,845 A | 2/1999 | Thalgott |
| 5,868,749 A | 2/1999 | Reed |
| 5,885,299 A | 3/1999 | Winslow et al. |
| 5,885,300 A | 3/1999 | Tokuhashi et al. |
| 5,888,219 A | 3/1999 | Bonutti |
| 5,888,222 A | 3/1999 | Coates |
| 5,888,227 A | 3/1999 | Cottle |
| 5,895,426 A | 4/1999 | Scarborough et al. |
| 5,895,428 A | 4/1999 | Berry |
| 5,899,939 A | 5/1999 | Boyce et al. |
| 5,904,683 A | 5/1999 | Pohndorf et al. |
| 5,904,719 A | 5/1999 | Errico et al. |
| 5,928,238 A | 7/1999 | Scarborough et al. |
| 5,941,882 A | 8/1999 | Jammet et al. |
| 5,968,047 A | 10/1999 | Reed |
| 5,972,368 A | 10/1999 | McKay |
| 5,980,522 A | 11/1999 | Koros et al. |
| 5,984,967 A | 11/1999 | Zdeblick et al. |
| 5,989,289 A | 11/1999 | Coates et al. |
| 6,025,538 A | 2/2000 | Yaccarino, III |
| 6,030,635 A | 2/2000 | Gertzman et al. |
| 6,045,554 A | 4/2000 | Grooms et al. |
| 6,045,579 A | 4/2000 | Hochshuler et al. |
| 6,045,580 A | 4/2000 | Scarborough et al. |
| 6,066,174 A | 5/2000 | Farris |

| | | |
|---|---|---|
| 6,077,267 A | 6/2000 | Huene |
| 6,083,225 A | 7/2000 | Winslow et al. |
| 6,090,143 A | 7/2000 | Meriwether et al. |
| 6,096,081 A | 8/2000 | Grivas et al. |
| 6,102,950 A | 8/2000 | Vaccaro |
| 6,111,164 A | 8/2000 | Rainey et al. |
| 6,113,637 A | 9/2000 | Gill et al. |
| 6,113,638 A | 9/2000 | Williams et al. |
| 6,123,705 A | 9/2000 | Michelson |
| 6,123,731 A | 9/2000 | Boyce et al. |
| 6,132,472 A | 10/2000 | Bonutti |
| 6,136,002 A | 10/2000 | Shih et al. |
| 6,139,211 A | 10/2000 | Schroeder et al. |
| 6,143,033 A | 11/2000 | Paul et al. |
| 6,156,037 A | 12/2000 | LeHuec et al. |
| 6,159,215 A | 12/2000 | Urbahns et al. |
| 6,174,311 B1 | 1/2001 | Branch et al. |
| 6,200,347 B1 | 3/2001 | Anderson et al. |
| 6,206,923 B1 | 3/2001 | Boyd et al. |
| 6,210,442 B1 | 4/2001 | Wing et al. |
| 6,235,059 B1 | 5/2001 | Benezech et al. |
| 6,258,125 B1 | 7/2001 | Paul et al. |
| 6,270,528 B1 | 8/2001 | McKay |
| 6,277,149 B1 | 8/2001 | Boyle et al. |
| 6,294,041 B1 | 9/2001 | Boyce et al. |
| 6,294,187 B1 | 9/2001 | Boyce et al. |
| 6,315,795 B1 | 11/2001 | Scarborough et al. |
| 6,326,018 B1 | 12/2001 | Gertzman et al. |
| 6,350,283 B1 | 2/2002 | Michelson |
| 6,379,385 B1 | 4/2002 | Kalas et al. |
| 6,383,221 B1 | 5/2002 | Scarborough et al. |
| 6,425,920 B1 | 7/2002 | Hamada |
| 6,432,107 B1 | 8/2002 | Ferree |
| 6,454,806 B1 | 9/2002 | Cohen et al. |
| 6,468,543 B1 * | 10/2002 | Gilbertson et al. ........ 424/198.1 |
| 6,527,773 B1 | 3/2003 | Lin et al. |
| 6,530,955 B2 | 3/2003 | Boyle et al. |
| 6,547,823 B2 | 4/2003 | Scarborough et al. |
| 6,569,168 B2 | 5/2003 | Lin |
| 6,579,321 B1 | 6/2003 | Gordon et al. |
| 6,638,310 B2 | 10/2003 | Lin et al. |
| 6,696,073 B2 | 2/2004 | Boyce et al. |
| 6,733,504 B2 | 5/2004 | Lin et al. |
| 6,855,167 B2 | 2/2005 | Shimp et al. |
| 6,863,694 B1 | 3/2005 | Boyce et al. |
| 6,911,045 B2 | 6/2005 | Shimp |
| 2001/0020186 A1 | 9/2001 | Boyce et al. |
| 2001/0043258 A1 | 11/2001 | Ohki |
| 2002/0029084 A1 | 3/2002 | Paul et al. |
| 2002/0045897 A1 | 4/2002 | Dixon et al. |
| 2002/0058950 A1 | 5/2002 | Winterbottom et al. |
| 2002/0128717 A1 | 9/2002 | Alfaro et al. |
| 2002/0161445 A1 | 10/2002 | Crozel |
| 2002/0188295 A1 | 12/2002 | Martz et al. |
| 2003/0039676 A1 | 2/2003 | Boyce et al. |
| 2003/0049326 A1 | 3/2003 | Nimni |
| 2003/0060825 A1 | 3/2003 | Alfaro et al. |
| 2003/0130667 A1 | 7/2003 | Lin |
| 2003/0135214 A1 | 7/2003 | Fetto et al. |
| 2003/0147860 A1 | 8/2003 | Marchosky |
| 2004/0024457 A1 | 2/2004 | Boyce et al. |
| 2004/0044409 A1 | 3/2004 | Alfaro et al. |
| 2004/0098129 A1 | 5/2004 | Lin |
| 2004/0146543 A1 | 7/2004 | Shimp et al. |
| 2004/0243242 A1 | 12/2004 | Sybert et al. |
| 2004/0249377 A1 | 12/2004 | Kaes et al. |
| 2005/0008620 A1 | 1/2005 | Shimp et al. |
| 2005/0008672 A1 | 1/2005 | Winterbottom et al. |
| 2005/0027033 A1 | 2/2005 | Knaack et al. |
| 2005/0038511 A1 | 2/2005 | Martz et al. |
| 2005/0107880 A1 | 5/2005 | Shimp et al. |
| 2005/0143740 A1 | 6/2005 | Morris et al. |
| 2005/0283255 A1 | 12/2005 | Geremakis et al. |
| 2006/0149376 A1 | 7/2006 | Shimp et al. |
| 2007/0178158 A1 | 8/2007 | Knaack et al. |

FOREIGN PATENT DOCUMENTS

| | | |
|---|---|---|
| DE | 2 253 086 | 10/1972 |
| DE | 40 12 622 C | 7/1991 |
| DE | 43 02 397 | 7/1993 |
| DE | 198 15 407 | 10/1999 |
| DE | 298 14 174 U | 12/1999 |
| EP | 0 302 719 | 2/1989 |
| EP | 0 307 241 | 3/1989 |
| EP | 0 325 566 | 7/1989 |
| EP | 0 332 826 | 9/1989 |
| EP | 0 493 698 | 7/1992 |
| EP | 0 732 093 | 2/1996 |
| EP | 0 734 703 | 10/1996 |
| EP | 1 064 890 | 1/2001 |
| FR | 2636227 | 3/1990 |
| FR | 2703580 | 10/1994 |
| FR | 2742652 | 6/1997 |
| FR | 2769827 | 4/1999 |
| JP | 01/179689 | 7/1989 |
| SU | 1107854 | 8/1984 |
| SU | 590872 A | 11/1985 |
| WO | WO 89/09035 | 10/1989 |
| WO | WO 93/01771 | 2/1993 |
| WO | WO-94/21298 | 9/1994 |
| WO | WO 97/15246 | 5/1997 |
| WO | WO 97/47258 | 12/1997 |
| WO | WO 98/02117 | 1/1998 |
| WO | WO 98/17209 | 4/1998 |
| WO | WO 98/48738 | 11/1998 |
| WO | WO 99/07312 | 2/1999 |
| WO | WO 99/09914 | 3/1999 |
| WO | WO 99/21515 | 5/1999 |
| WO | WO 99/38461 | 8/1999 |
| WO | WO 00/07527 | 2/2000 |
| WO | WO 00/24327 | 5/2000 |
| WO | WO 00/40177 | 7/2000 |
| WO | WO 00/40179 | 7/2000 |
| WO | WO 01/00792 A1 | 1/2001 |
| WO | WO 01/49220 | 7/2001 |
| WO | WO 01/66048 | 9/2001 |
| WO | WO 01/70136 | 9/2001 |
| WO | WO 01/70137 | 9/2001 |
| WO | WO 01/70139 | 9/2001 |
| WO | WO 01/78798 | 10/2001 |
| WO | WO 03/030956 A2 | 4/2003 |
| WO | WO-2005/072656 | 8/2005 |

OTHER PUBLICATIONS

*Allograft Freeze-Dried Release Specifications*, Osteotech, Inc., Sep. 30, 1992, 3 pages.

Brantigan, J.W., DePuy AcroMed, Lumbar I/F Cage With VSP Spinal System (Surgical Technique) (1999).

DePuy AcroMed, Lumbar I/F Cage Implants & Instruments (Product Catalog) (1999).

Frymoyer et al., Eds., "The Adult Spine Principles and Practice," *Poster Lumbar Interbody Fusion*, James W. Simmons, vol. 2, pp. 1961-1987 (1991).

Gerhart et al. "Biomechanical optimization of a model particulate composite for orthopaedic applications," *J. Orthop. Res* (1986); 4(1): 86-85 [abstract only].

Lewandrowski et al., "Improved Osteoinduction of Cortical Bone Allografts: A Study of the Effects of Laser Perforation and Partial Demineralization," *J. Ortho Res*. 15:748-756 (1997).

Ma, G.W.C., Posterior Lumbar Interbody Fusion with Specialized Instruments, *Clinical Ortho and Rel. Res.*, 193 (March) pp. 57-63 (1985).

McCord et al., "Anterior endoscopic thoracolumbar instrumentation and implants," *Curr. Ortho 12*, pp. 96-103 (1998).

Smith, MD et al. "Load-bearing capacity of corticocancellous bone grafts in the spine" (truncated abstract), Aug. 1993, *Journal of Bone & Joint Surgery*, 75(8): 1206-13.

Stevenson, S., "Enhancement of Fracture Healing with Autogenous and Allogeneic Bone Grafts," *Clin. Ortho, Rel. Res*. 355S, pp. S239-S246 (1998).

Tan et al., A modified technique of anterior Lumbar fusion with femoral cortical allograft; *J. Orthop. Surg. Tech*; vol. 5, No. 3 91990), pp. 83-93.

VG2 Interbody Bone Grafts, DuPuy AcroMed, 2000, 6 pages.

Vich, Jose M. Otero, "Anterior cervical interbody fusion with threaded cylindrical bone," *J. Neurosurg.* 63:750-753, 1985.

Crowe et al., "Inhibition of Enzymic Digestion of Amylose by Free Fatty Acids In Vitro Contributes to Resistant Starch Formation", *J. Nutr.*, 130(8): 2006-8, 2000.

Edwards et al., "Osteoinduction of Human Demineralized Bone: Characterization in a Rat Model", *Clinical Orthopaedics & Rel. Res.*, 357: 219-228, 1998.

Glowacki et al., "Demineralized Bone Implants", *Clinics in Plastic Surgery*, 12(2): 233-41, 1985.

Han et al., "Quantitative and sensitive in vitro assay for osteoinductive activity of demineralized bone matrix", *J. Orthop. Res.*, 21(4):648-54, 2003.

Jain et al., "Anchoring of phospholipase A2: the effect of anions and deuterated water, and the role of N-terminus region", *Biochem. et Biophys. Acta*, 860: 448-61, 1986.

Katz, "The biology of heavy water", *Scientific American*, 106-116, 1960.

Mulliken et al., "Fate of Mineralized and Demineralized Osseous Implants in Cranial Defects.", *Calcif. Tissue Int.*, 33: 71-6, 1981.

Neigel et al., "Use of Demineralized Bone Implants in Orbital and Craniofacial Reconstruction and a Review of the Literature", *Opthal. Plast. Reconstr. Surg.*, 12(2): 108-20, 1996.

Ray et al., "Bone implants", *J. Bone & Joint Surgery*, 39-A(5):1119-28, 1957.

Russell et al., "Clinical Utility of Demineralized Bone Matrix for Osseous Defects, Arthrodesis, and Reconstruction: Impact of Processing Techniques and Study Methodology", *Orthopaedics*, 22(5): 524-31, 1999.

Ueland et al., "Increased cortical bone content of insulin-like growth factors in acromegalic patients", *J. Clin. Endocrinol.& Metab.*, 84(1): 123-7, 1999.

Urist, "Bone: formation by autoinduction", *Science*, 150: 893-99, 1965.

Urist et al., "Observations Implicating an Extracellular Enzymic Mechanism of Control of Bone Morphogenesis", *J. Histochem. & Cytochem.*, 22(2): 88-103, 1974.

Urist et al., "Preservation and biodegradation of the morphogenetic property of bone matrix." *J. Theor. Biol.*, 38: 155-67, 1973.

Whiteman et al., "Demineralized Bone Powder: Clinical applications for bone defects of the hand", *J. Hand. Surg (British and European Volume)*, 18B: 487-90, 1993.

Xiaobo et al., "Experimental and Clinical Investigations of Human Insoluble Bone Matrix Gelatin", *Clin. Orthop. & Rel. Res.*, 293: 360-5, 1993.

Zhang et al., "A Quantitative Assessment of Osteoinductivity of Human Demineralized Bone Matrix", *J. Periodontol.*, 68(11): 1076-84, 1997.

International Searching Authority, "International Search Report," PCT Application No. PCT/US05/003092, mailed on Jun. 23, 2005, 3 pgs.

International Searching Authority, "Written Opinion," PCT Application No. PCT/ US05/003092, mailed on Jun. 23, 2005, 3 pgs.

* cited by examiner

NON-GLYCEROL STABILIZED BONE GRAFT

RELATED APPLICATIONS

The present application claims priority under 35 U.S.C. §120 to international PCT application PCT/US2005/003092, filed Jan. 27, 2005, which claims priority under 35 U.S.C. §119(e) to U.S. provisional patent application U.S. Ser. No. 60/539,555, filed Jan. 27, 2004, each of which is incorporated herein by reference in its entirety.

BACKGROUND

The rapid and effective repair of bone defects caused by injury, disease, wounds, surgery, etc., has long been a goal of orthopaedic surgery. Toward this end, a number of compositions and materials have been used or proposed for use in the repair of bone defects. The biological, physical, and mechanical properties of the compositions and materials are among the major factors influencing their suitability and performance in various orthopaedic applications.

Autologous cancellous bone ("ACB") is considered the gold standard for bone grafts. ACB is osteoinductive, is non-immunogenic and, by definition, has all of the appropriate structural and functional characteristics appropriate for the particular recipient. Unfortunately, ACB is only available in a limited number of circumstances. Some individuals lack ACB of appropriate dimensions and quality for transplantation. Moreover, donor site morbidity can pose serious problems for patients and their physicians.

Much effort has been invested in the identification or development of alternative bone graft materials. Demineralized bone matrix ("DBM") implants have been reported to be particularly useful (see, for example, U.S. Pat. Nos. 4,394,370; 4,440,750; 4,485,097; 4,678,470; and 4,743,259; Mulliken et al., *Calcif. Tissue Int.* 33:71, 1981; Neigel et al., *Opthal. Plast. Reconstr. Surg.* 12:108, 1996; Whiteman et al., *J. Hand. Surg.* 18B:487, 1993; Xiaobo et al., *Clin. Orthop.* 293:360, 1993; each of which is incorporated herein by reference). Demineralized bone matrix is typically derived from cadavers. The bone is removed aseptically and/or treated to kill any infectious agents. The bone is then particulated by milling or grinding and then the mineral component is extracted (e.g., by soaking the bone in an acidic solution). The remaining matrix is malleable and can be further processed and/or formed and shaped for implantation into a particular site in the recipient. Demineralized bone prepared in this manner contains a variety of components including proteins, glycoproteins, growth factors, and proteoglycans. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient. In addition to the active factors present within the DBM, the overall structure of the DBM implant is also believed to contribute to the bone healing capabilities of the implant.

Current DBM formulations have various drawbacks. First, while the collagen-based matrix of DBM is relatively stable, the active factors within the DBM matrix are rapidly degraded. The osteogenic activity of the DBM may be significantly degraded within 24 hours after implantation, and in some instances the osteogenic activity may be inactivated within 6 hours. Therefore, the factors associated with the DBM are only available to recruit cells to the site of injury for a short time after transplantation. For much of the healing process, which may take weeks to months, the implanted material may provide little or no assistance in recruiting cells. Second, the current DBM formulations have a limited shelf-life due to the degradatory enzymes present in DBM preparations.

There remains a need to develop improved bone graft materials with greater and/or longer osteoinductive activity. These improved preparations should also have a longer shelf-life than current preparations.

SUMMARY OF THE INVENTION

The present invention provides stabilized demineralized bone matrix ("DBM") compositions, related methods for preparing and using the inventive compositions, and kits containing the inventive compositions. In light of the degradation of osteoinductive agents by enzymes endogenous to the DBM (e.g., proteases), the present invention provides DBM compositions in which the activity of endogenous enzymes on osteoinductive agents is lowered by (1) decreasing the pH of the DBM composition; (2) removing water from the DBM composition, and optionally, coating the dehydrated DBM particles to prevent water from rehydrating it; (3) increasing the concentration of deuterated water in the DBM composition; (4) adding protease inhibitors to the DBM composition; (5) adding a water substitute to the DBM composition; and/or (6) modifying covalently the osteoinductive factors in the DBM. The DBM of the stabilized DBM compositions may be provided in any form including fibers, plates, particles (e.g., cubes, spheres, cones, wedges, irregular particles, etc.), threads, gels, etc. One or more of these strategies described above may be used to prepare a DBM composition with a desired shelf life, e.g. at least 90% of the original osteoinductive activity remaining after 1 year at room temperature.

In one aspect the pH of the inventive DBM composition is lowered, the acidic environment of inventive DBM compositions slows the proteolysis of osteoinductive factors within the DBM compositions, resulting in a DBM composition with a longer shelf-life. DBM compositions with an acidic pH (e.g., pH 2, 3, 4, 5, or 6) have increased stability when compared to DBM compositions at physiologic pH. In certain preferred embodiments, the acidified DBM composition retains greater than 75% of its original osteoinductivity after 6 months or 1 year of storage at room temperature. This increased shelf-life can be further extended by storing the DBM composition at a lower temperature such as 4° C. The biological activity of acidified DBM compositions may be further stabilized by the addition of protease inhibitors (see U.S. patent application, U.S. Ser. No. 10/271,140, filed Oct. 15, 2002; incorporated herein by reference) and/or water substitutes such as deuterated water ($D_2O$), DMSO, and polyols (e.g., glycerol) to the composition. In addition, acidified DBM compositions may be further stabilized by the addition of stabilizing agents such as those described in U.S. Ser. No. 10/271,140, filed Oct. 15, 2002, incorporated herein by reference (e.g., proteins, polymers, hydrogels, collagen, sugars, amino acids, lipids, etc.).

The factors in DBM responsible for osteoinductivity are susceptible to degradation by endogenous enzymes found in the DBM, especially in hydrated DBM compositions. DBM compositions, therefore, may be stored in partially or fully dehydrated forms by lyophilizing the composition. In lyophilized form, the osteoinductivity of DBM compositions is stable even when the composition is stored at room temperature. This stabilizing effect can be further increased by storing the DBM composition at lower temperatures. Lyophilization of the DBM composition can be performed on acidified DBM compositions as well as DBM compositions with sugars, polymers, lipids, water substitutes such as polyols and deuterated water, or protease inhibitors added.

Water substitutes such as deuterated water ($D_2O$), glycerol, flowable polymers, flowable lipids, or polyols may also be used to decrease the degradation of the factors in DBM responsible for its biological activity. For example, the addition of deuterated water ($D_2O$) has been found to inhibit the enzymes responsible for degrading the osteodinductive agents found in DBM compositions. By increasing the $D_2O$ content in DBM compositions the degrading enzymes are inhibited, and the DBM compositions have a longer shelf-life. The concentration of $D_2O$ in the inventive DBM compositions may range from 5% up to 98%, preferably 10% to 80%, more preferably 20% to 75%. The stabilizing effect of $D_2O$ may be combined with acidifying the DBM composition, dehydrating the composition, adding protease inhibitors, adding a polymer, adding a lipid, and/or adding other water substitutes.

The inventive DBM composition can be further stabilized by encapsulating DBM with stabilizing agents (e.g., proteins, polymers, hydrogels, collagen, sugars, amino acids, lipids, etc.). Encapsulating the DBM or adding a flowable carrier to the DBM prior to, during, or after hydration slows the proteolysis of osteoinductive factors within the DBM compositions resulting in a DBM composition with a longer shelf-life. Particles in a dry DBM are coated, encapsulated, or otherwise associated with a lipid or other agent (e.g., polymer) to protect the osteoinductive agents from being degraded in the presence of water. For example, the DBM may be dehydrated and then coated with a lipid or polymer to prevent water from re-hydrating the DBM. This allows for water or another carrier to be added back to the DBM composition without a loss in stability. Aqueous carriers or water may be added to produce a composition with the desired consistency and handling properties. The percentage of particles in the DBM, which are treated with the lipid or polymer, ranges from 10% up to 100%. The stabilizing effect of the agents may be enhanced further by acidifying the DBM composition, adding a protease inhibitor, and/or adding a water substitute such as deuterated water ($D_2O$).

In another aspect, the present invention provides methods of preparing inventive stabilized DBM compositions. For instance, the present invention provides methods of formulating a DBM composition with a shelf-life of 6 months, 1 year, 2 years, 3 years, 5 years, or 10 years. In one embodiment, the pH of the inventive DBM composition is reduced by rinsing or soaking the DBM in a solution of the desired acidic pH. Optionally, the acidified DBM composition may be lyophilized to reduce the water content of the composition. Deuterated water, other water substitutes, or agents such as lipids and polymers may be added to the inventive DBM compositions during the preparation process to further stabilize and prevent the degradation of the osteoinductive agents. In certain embodiments, the composition is prepared with a carrier to make it flowable.

The present invention also provides kits for preparing and using the inventive DBM compositions The kits may be used to treat bone defects using the inventive DBM compositions. For example, the DBM composition may be provided as a paste in a delivery device such as a syringe for use in a clinical setting. The DBM composition is preferably flowable for ease in using the composition. Preferably, the DBM composition is sterile and is packaged so that it can be applied under sterile or aseptic conditions (e.g., in an operating room).

The present invention further provides a system for characterizing DBM compositions, and for identifying and preparing DBM-containing compositions with improved properties. For example, the invention provides methods of assessing the osteoinducitivity of DBM compositions. The invention also provides methods of determining the shelf-life of DBM compositions.

DEFINITIONS

Figure 1:
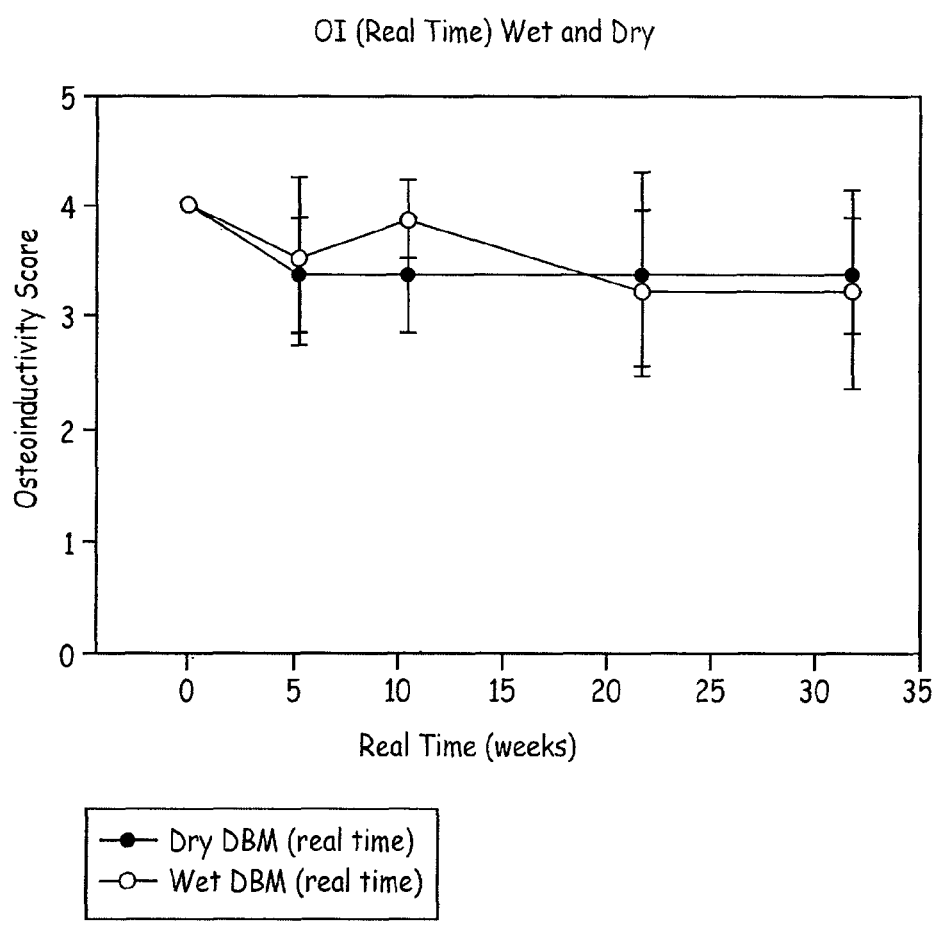
FIG. 1. Comparison of the osteoinductivity of hydrated (wet) DBM and dry (lyophilized) DBM compositions at room temperature.
Figure 2:
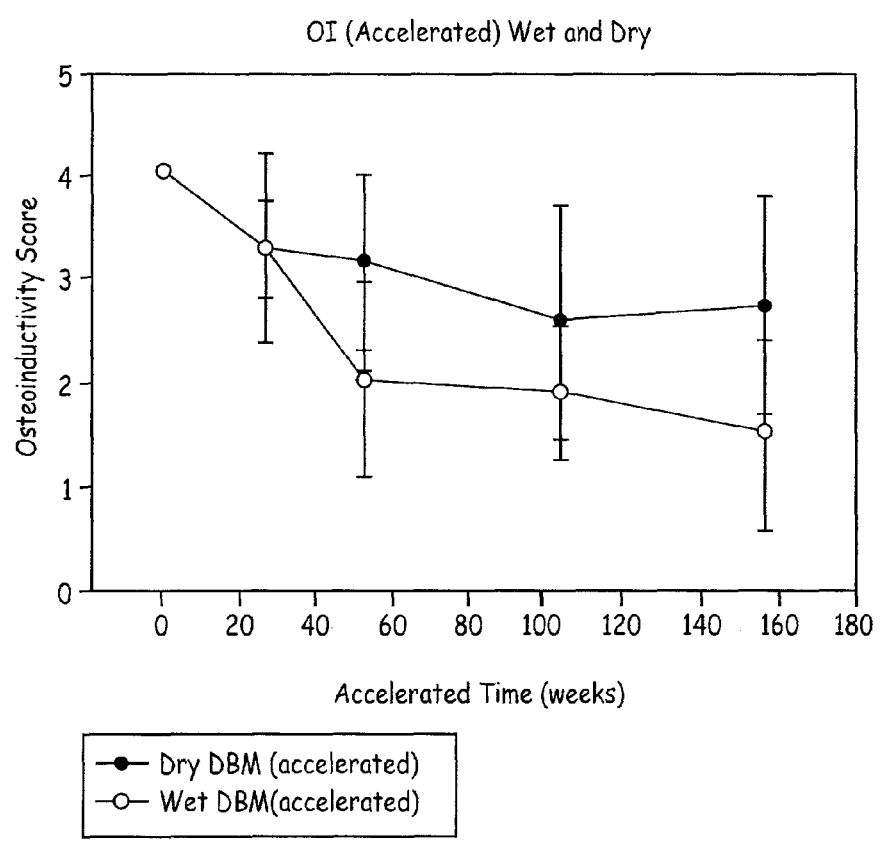
FIG. 2. Comparison of the osteoinductivity of hydrated (wet) and dry (lyophilized) DBM compositions with accelerated aging at 40° C.

Acidic or acidified: An acidic or acidified DBM or DBM compositions is any composition in which the pH of the matrix has been decreased below physiologic pH (pH 7.4). The acidification may be accomplished using any method known in the art including soaking or rinsing the DBM in an acidic solution (e.g., a solution of HCl, acetic acid, EDTA, phosphoric acid, carboxylic acids, etc.). In other embodiments, a buffered solution may be used to acidify the DBM. Preferably, the soaking or rinsing is performed sufficiently to achieve the desired lower pH in inner portions of the DBM particles, and preferably substantially throughout the particles. In certain preferred embodiments, the pH is reduced to between 2 and 6. More preferably, the pH of the DBM is between 3 and 4. In other embodiments, the desired lower pH is approximately 6.5, 6, 5.5, 5, 4.5, 4, 3.5, 3, 2.5, 2, 1.5, or 1.

Associated with: A stabilizing agent, targeting agent, or other chemical entity is associated with DBM or other osteogenic matrix according to the present invention if it is retained by the implant long enough to significantly affect the osteoinductivity, stability, or other property of the implant (e.g., increase the osteoinductive score of a composition). Specific examples include 1) not freely diffusible from the DBM as determined in in vitro diffusion assays in simulated body fluids; and/or 2) has an extended half-life (e.g., at least 10%, 20%, 30%, 40%, 50%, 100% longer) in the DBM as compared with free in solution. In some embodiments, associations are covalent; in others they are non-covalent. Examples of non-covalent interactions include physical embedding, electrostatic interactions, hydrogen bonding, hydrophobic interactions, pi-pi stacking, and van der Waals interactions. For instance, a bioactive agent may be rendered associated with a DBM or other inventive matrix by virtue of a polymeric stabilizing agent that restrains diffusion of the bioactive agent from the matrix. Alternatively or additionally, the bioactive agent may be rendered associated with a DBM by virtue of a physical interaction with one or more entities that are themselves associated with the DBM.

Biocompatible: The term biocompatible as used herein is intended to describe materials that, upon administration in vivo, do not induce undesirable long term effects.

Biodegradable: As used herein, biodegradable materials are materials that degrade under physiological conditions to form a product that can be metabolized or excreted without damage to organs. Biodegradable materials are not necessarily hydrolytically degradable and may require enzymatic action to fully degrade. Biodegradable materials also include materials that are broken down within cells.

Demineralized bone activity refers to the osteoinductive and/or osteoconductive activity of demineralized bone.

Demineralized bone matrix, as used herein, refers to any material generated by removing mineral material from living bone tissue. In preferred embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the invention.

Diffusion barrier refers to any material, coating, film, or substance that decreases the rate of diffusion of a substance from one side of the barrier to the other side, and more specifically, from outside to in or vice versa. The diffusion barrier in certain embodiments may be a polymer including proteins, polysaccharides, cellulose, man-made polymer, PLGA, etc. that prevents the diffusion of activating agents (including water, enzymes, etc.) and/or degradatory enzymes into the DBM composition. The diffusion barrier may also prevent the movement of osteoinductive factors out of the DBM composition. In certain embodiments, the diffusion barrier is biodegradable, leading to the degradation, activation, or release of osteoinductive factors over an extended period of time. In other embodiments, the diffusion barrier may segmentally and/or regionally degrade to control the release rates in certain regions of the composition. For a more detailed description of diffusion barriers useful in stabilizing DBM compositions, see U.S. Ser. No. 10/271,140, filed Oct. 15, 2002; U.S. Ser. No. 60/392,462, filed Jun. 27, 2002; and U.S. Ser. No. 60/329,156, filed Oct. 12, 2001; each of which is incorporated herein by reference.

Matrix, as used herein, refers to a natural or synthetic vehicle capable of association with at least one growth factor for delivery to an implant site. The matrix may be completely insoluble or may be slowly solubilized after implantation. Following implantation, preferred matrices resorb or degrade slowly, remaining substantially intact for at least one to seven days, most preferably for two or four weeks or longer and often longer than 60 days. Growth factors may be endogenously present in the matrix as in the case of most demineralized bone, or they may be exogenously added to the matrix. Matrices may also include combinations of endogenous and exogenous growth factors. The matrix may be in particulate or fiber form, or may be monolithic. The matrix may comprise a number of materials and forms in combination such as fibers and particles. In one preferred embodiment, the matrix is comprised of heat pressed demineralized bone fibers. In other embodiments, the matrix comprises resorbable plastic polymers such as those described below as suitable for use as diffusion barriers. In certain embodiments, the polymer imparts rigidity upon the inventive composition. In other preferred embodiments, a particulated amorphous calcium phosphate is used as the matrix in association with an adsorbed growth factor such as a BMP, (more specifically BMP-2 or BMP-4 or derivatives thereof). Still other matrix embodiments requiring the addition of an exogenous growth factor include, but are not limited to, particulated ceramics, preferably calcium sulphates or calcium phosphates. The most preferred matrices are calcium phosphates, the preparation of which is well known to practitioners in the art (see, for example, Driessens et al. "Calcium phosphate bone cements" Wise, D. L., Ed. *Encyclopedic Handbook of Biomaterials and Bioengineering, Part B, Applications* New York: Marcel Decker; Elliott *Structure and Chemistry of the Apatites and Other Calcium Phosphates* Elsevier, Amsterdam, 1994; each of which is incorporated herein by reference). Also, advantageous are settable calcium phosphate preparations such as α-BSM (ETEX Corp., Cambridge, Mass.). Calcium phosphate matrices include, but are not limited to, dicalcium phosphate dihydrate, monetite, tricalcium phosphate, tetracalcium phosphate, hydroxyapatite, nanocrystalline hydroxyapatite, poorly crystalline hydroxyapatite, substituted hydroxyapatite, and calcium deficient hydroxyapatites.

Osteoinductive, as used herein, refers to the quality of being able to stimulate bone formation. Any material that can induce the formation of ectopic bone in the soft tissue of an animal is considered osteoinductive. For example, most osteoinductive materials induce bone formation in athymic rats when assayed according to the method of Edwards et al. ("Osteoinduction of Human Demineralized Bone: Characterization in a Rat Model" *Clinical Orthopeadics & Rel. Res.,* 357:219-228, December 1998; incorporated herein by reference). Osteoinductivity in some instances is considered to occur through cellular recruitment and induction of the recruited cells to an osteogenic phenotype. Osteoinductivity may also be determined in tissue culture as the ability to induce an osteogenic phenotype in culture cells (primary, secondary, or explants). It is advisable to calibrate the tissue culture method with an in vivo ectopic bone formation assay as described by Zhang et al. "A quantitative assessment of osteoinductivity of human demineralized bone matrix" *J. Periodontol.* 68(11): 1076-84, November 1997; incorporated herein by reference. Calibration of the in vitro assays against a proven in vivo ectopic bone formation model is critical because the ability of a compound to induce an apparent "osteogenic" phenotype in tissue culture may not always be correlated with the induction of new bone formation in vivo. BMP, IGF, TGF-β, parathyroid hormone (PTH), and angiogenic factors are only some of the osteoinductive factors found to recruit cells from the marrow or perivascular space to the site of injury and then cause the differentiation of these recruited cells down a line responsible for bone formation. DBM isolated from either bone or dentin have both been found to be osteoinductive materials (Ray et al., "Bone implants" *J. Bone Joint Surgery* 39A:1119, 1957; Urist, "Bone: formation by autoinduction" *Science* 150:893, 1965; each of which is incorporated herein by reference).

Osteoinductivity score refers to a score ranging from 0 to 4 as determined according to the method of Edwards et al. (1998) or an equivalent calibrated test. In the method of Edwards et al., a score of "0" represents no new bone formation; "1 " represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, for the improved inventive formulations, particularly those with osteoinductivity comparable to the BMPs, the osteoinductive score may be obtained at earlier time points such as 7, 14, or 21 days following implantation. In these instances it is important to include a normal DBM control such as DBM powder without a carrier, and if possible, a positive control such as BMP. Occasionally osteoinductivity may also be scored at later timepoints such as 40, 60, or even 100 days following implantation. Percentage of osteoinductivity refers to an osteoinductivity score at a given time point expressed as a percentage of activity, of a specified reference score. Alternatively, a quantitative and sensitive in vitro assay for osteoinductive activity of demineralized bone matrix to check the bone-forming potential of demineralized bone matrix (DBM) is used. The osteoinductivity of the bone morphogenic proteins (BMPs), present in DBM, can be measured in vitro using a pluripotent myoblast C2C12 cell line. Alkaline phosphatase activity induced by co-incubation of DBM with C2C12 cells was dose-responsive and corresponds to the amount of active BMPs in DBM. Bone forming potential was simultaneously tested in vivo by implanting DBM intramuscularly in nude rats. Alkaline phosphatase activity induced in C2C12 cells, correlated with bone formation in vivo (r=0.88), determined by alkaline phosphatase activity, mineralization density, and histomorphology of the DBM explants. Results from DBM batches, originating from five established bone banks, showed good consistency between in vitro and in vivo assays. However, DBM activity varied widely from bank to bank as well as from batch to batch within the same bank (Han et al. *J. Orthop. Res.* 21(4):648-54 (July 2003); incorporated herein by reference).

Particle or fibers refers to a preparation of DBM, DBM compositions, or bone sample that has been milled, ground, pulverized, or otherwise reduced to a particulate form. The size of the particles or fibers is typically greater than 50 microns, preferably greater than 75 microns, more preferably greater than 100 microns, and most preferably greater than 150 microns. These dimensions refer to average particle diameter for more spherical-like particles, and for particles of other shapes except where specifically indicated it refers to the smallest cross-sectional dimension of the particle. In certain embodiments, the composition may include even larger sized particles, preferably greater than 1 mm, greater than 1.5 mm, or most preferably greater than 2 mm in their largest dimension. The particles or fibers may be of any shape including wedges, rods, spheres, cubes, discs, ovals, coils, coiled coils, irregularly shaped, etc. For example, in certain embodiments, the particles may be wedge-shaped and be approximately 2 mm in their largest dimension and 100 microns or less in another dimension. The particles or fibers may be sieved or sorted in order to collect particles of a particular size. These particles or fibers may be mixed with a solution, slurry, deformable solid, or liquid to form a paste to be used in administering or applying the graft of DBM, inventive DBM composition, or bone sample. Preferred methods of particle or fiber preparation are disclosed in issued U.S. Pat. Nos. 5,607,269; 5,236,456; 5,284,655; 5,314,476; and 5,507,813; each of which is incorporated herein by reference.

Polyol refers to any polymer having at least one hydroxyl group per repeating unit. In certain instances, a polyol has two, three, four, or more hydroxyl groups per repeating unit. Polyols may be natural or unnatural polymers. Natural polyols include polysaccharides. Unnatural polyols include polyvinyl alcohol and polyethylene glycol. Examples of polyols include polyvinyl alcohols, polyethylene glycols, erythritol, hydrogenated starch hydrolysates, isomalt, lactitol, maltitol, mannitol, sorbitol, and xylitol. In certain embodiments, polyols are used as water substitutes in DBM compositions.

Polysaccharide, as used herein, refers to any polymer or oligomer of carbohydrate residues. The polymer may consist of anywhere from two to hundreds to thousands of sugar units. Polysaccharides may be purified from natural sources such as plants or may be synthesized de novo in the laboratory. Polysaccharides isolated from natural sources may be modified chemically to change their chemical or physical properties (e.g., phosphorylated, cross-linked). Polysaccharides may also be either straight or branch-chained. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

Protease inhibitors, as used herein, are chemical compounds capable of inhibiting the enzymatic activity of protein cleaving enzymes (i.e., proteases). The proteases inhibited by these compounds include serine proteases, acid proteases, metalloproteases (examples of some matrix metalloprotease inhibitors are shown in FIG. 6), carboxypeptidase, aminopeptidase, cysteine protease, etc. The protease inhibitor may act specifically to inhibit only a specific protease or class of proteases, or it may act more generally by inhibiting most if not all proteases. Preferred protease inhibitors are protein or peptide based and are commercially available from chemical companies such as Sigma-Aldrich. Protein or peptide-based inhibitors which adhere to the DBM (or calcium phosphate or ceramic carrier) are particularly preferred as they remain associated with the matrix providing a stabilizing effect for a longer period of time than freely diffusible inhibitors. Examples of protease inhibitors include aprotinin, 4-(2-aminoethyl)beiizenesulfonyl fluoride (AEBSF), amastatin-HCl, alpha1-antichymotrypsin, antithrombin III, alpha1-antitrypsin, 4-aminophenylmethane sulfonyl-fluoride (APMSF), arphamenine A, arphamenine B, E-64, bestatin, CA-074, CA-074-Me, calpain inhibitor I, calpain inhibitor II, cathepsin inhibitor, chymostatin, diisopropylfluorophosphate (DFP), dipeptidylpeptidase IV inhibitor, diprotin A, E-64c, E-64d, E-64, ebelactone A, ebelactone B, EGTA, elastatinal, foroxymithine, hirudin, leuhistin, leupeptin, alpha2-macroglobulin, phenylmethylsulfonyl fluoride (PMSF), pepstatin A, phebestin, 1,10-phenanthroline, phosphoramidon, chymostatin, benzamidine HCl, antipain, epsilon-aminocaproic acid, N-ethylmaleimide, trypsin inhibitor, 1-chloro-3-tosylamido-7-amino-2-heptanone (TLCK), 1-chloro-3-tosylamido-4-phenyl-2-butanone (TPCK), trypsin inhibitor, sodium EGTA, and sodium EDTA.

A peptide or protein, according to the present invention, comprises a string of at least two amino acids linked together by peptide bonds. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc.

Stabilizing agent is any chemical entity that, when included in an inventive composition comprising DBM and/or a growth factor preserves or extends the lifetime of the osteoinductive activity of the composition, as measured against a specified reference sample. In most cases, the reference sample will not contain the stabilizing agent, but in all other respects will be the same as the composition with stabilizing agent. The stabilizing agent also generally has little or no osteoinductivity of its own and works either by increasing the half-life of one or more of the active entities within the inventive composition as compared with an otherwise identical composition lacking the stabilizing agent. In other embodiments, the stabilizing agent may be a chemical compound that inhibits the activity of endogenous proteases or sugar-degrading enzymes. In a preferred embodiment, the stabilizing agent retards the access of one or more enzymes known to degrade one or more active factors. Half-life may be determined by immunolgical or enzymatic assay of a specific factor, either as attached to the matrix or extracted therefrom. Alternatively, measurement of an increase in osteoinductivity half-life, or measurement of the enhanced appearance of products of the osteoinductive process (e.g., bone, cartilage or osteogenic cells, products or indicators thereof such as levels of gene expression associated with bone cartilage formation) is a useful indicator of stabilizing effects for an enhanced osteoinductive matrix composition. The measurement of prolonged or enhanced osteoinductive response will generally be indicative of an increase in stability of a factor. For a more detailed description of stabilizing agents useful in stabilizing DBM compositions, see U.S. Ser. No. 10/271,140, filed Oct. 15, 2002; U.S. Ser. No. 60/392,462, filed Jun. 27, 2002; and U.S. Ser. No. 60/329,156, filed Oct. 12, 2001; each of which is incorporated herein by reference.

Stabilizing means refers to any manipulation of a formulation which improves its shelf-life stability either as measured at room temperature or under accelerated conditions. Preferred stabilizing means for the inventive DBM compositions include: limiting, reducing, or eliminating the availability of water to promote degradation of biological activity during storage, addition of thermodynamic stabilizers such as polyols, and the use of protease inhibitors.

Water substitute is any liquid or flowable chemical entity which can act as a substitute for water in a DBM composition. Typically, this means to provide a desired handling quality to the DBM composition. In certain embodiments, the water substitute may be a liquid or semi-solid. A water substitute typically has hydroxyl moieties to mimic the water molecule. Preferably, the water substitute has multiple hydroxyl groups. Examples of water substitutes include glycerol, carbohydrates, polysaccharides, polyols, polyethylene glycol, polyvinyl alcohol, hyaluronic acid, glycoproteins, deuterated water ($D_2O$), liquid polymers, liquid lipids, etc. Water substitutes may be added to increase the viscosity of an aqueous mixture such as a DBM composition. Water substitutes may be added to DBM compositions to stabilize the composition by increasing the viscosity of the water component of the composition or by decreasing the activity of the water present in the composition.

DESCRIPTION OF CERTAIN PREFERRED EMBODIMENTS

As described herein, the present invention provides compositions and methods relating to improved DBM compositions. Below, certain aspects of preferred embodiments of the invention are described in more detail and with reference to the Figures of the Drawing. Those of ordinary skill will appreciate that a variety of embodiments or versions of the invention are not specifically discussed below but are nonetheless within the scope of the present invention, as defined by the appended claims.

DBM is comprised principally of proteins and glycoproteins, collagen being the primary protein substituent of DBM. While collagen is relatively stable, being degraded only by the relatively rare collagenase enzymes, the other proteins and active factors present in DBM are relatively labile subject to degradation by enzymes endogenous to the DBM or other inactivating processes. The instant invention stabilizes the osteoinductivity of DBM compositions by slowing the degradation of the osteoinductive factors present in DBM. The instant invention also may increase the effective osteoinductivity of the DBM composition by reducing proteolytic degradation of the active factor within the DBM composition.

The instant invention provides several approaches to the protection of active factors from degradation by either host-derived or endogenous enzymes. Factors to be protected may be endogenous to DBM preparations or factors added to either DBM or synthetic matrix compositions. Protection is provided by lowering the pH of the DBM composition thereby inhibiting the degradatory activity of endogenous enzymes; and/or by reducing, minimizing, or eliminating in DBM preparations, the amount of water available to inactivate the active factors within DBM, through chemical or enzymatic processes. Available water is reduced by increasing the concentration of $D_2O$ to inhibit endogenous degrading enzymes; and/or adding water substitutes such as glycols, polyols, hyaluronic acid, etc.; and/or adding water diffusion barriers. The addition of chemical and/or enzymatic inhibitors (e.g., protease inhibitors) which prevent the degrading activity of hydrolysis and endogenous enzymes is also considered part of the instant invention. Water may be removed from the inventive stabilized DBM compositions to further stabilize the composition. Other methods of prolonging or stabilizing osteoinductivity may be used in conjunction with the inventive method. Preferably, the degradation of active factors within the DBM composition is inhibited to yield a desired osteoinductivity score after storage. These strategies for stabilizing DBM compositions are used to extend the shelf-life of DBM compositions so that more than 50%, generally more than 75%, and often more than 90% of the osteoinductivity of the original sample remains after one year at room temperature.

Demineralized Bone Matrix

DBM preparations have been used for many years in orthopaedic medicine to promote the formation of bone. For example, DBM has found use in the repair of fractures, in the fusion of vertebrae, in joint replacement surgery, in dental surgery, and in treating bone destruction due to underlying disease such as rheumatoid arthritis. DBM is thought to promote bone formation in vivo by osteoconductive and osteoinductive processes. Osteoconduction occurs if the implanted material serves as a scaffold for the support of new bone growth. Osteoconduction is particularly significant when bone growth is desired across a large or "critical size" defect, across which bone healing would proceed only slowly or not at all. It is generally believed that the osteoconductive properties of DBM preparations are provided by the actual shape and coherence of the implant. Thus DBM compositions comprising entangled fibers tend to have superior osteoconductive properties as compared to less fibrous, more granular preparations. Agents, carriers, or excipients, which tend to preserve the shape and/or coherence of the DBM substituent, can lead to better bone forming properties.

The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors, inherently present in DBM, which would be protected through the invention herein described.

Any of a variety of demineralized bone matrix preparations may be utilized in the practice of the present invention. DBM prepared by any method may be employed including particulate or fiber-based preparations, mixtures of fiber and particulate preparations, fully or partially demineralized preparations, mixtures of fully and partially demineralized preparations, including surface demineralized preparations as described by Gertzman et al. (U.S. Pat. No. 6,326,018, issued Dec. 4, 2001; incorporated herein by reference). Preferred DBM compositions are described by Dowd et al., U.S. Pat. No. 5,507,813, which is incorporated herein by reference. Also useful are DBM preparations comprising additives or carriers such as glycerol, polyhydroxyl compounds, polyols, polysaccharides, glycosaminoglycan proteins, hyaluronic acid, collagen, lipids, nucleic acids, polymers, polaxomers, resins, clays, calcium salts, and/or derivatives thereof. In certain embodiments, the carrier is a non-glycerol carrier. In other embodiments, the carrier is glycerol. The carriers added to the demineralized bone matrix may stabilize the composition and prevent the degradation of osteogenic factors. For example, the carrier may act as a diffusion barrier or water substitute.

In certain embodiments, the DBM material utilized to formulate inventive compositions has greater than 50%, preferably greater than 75%, more preferably greater than 80%, 85%, 90%, or 95% and most preferably greater than 98% of the calcium phosphate removed. The bone used in creating the DBM may be obtained from any source of living or dead tissue. Often, it will be preferred that the source of bone be matched to the eventual recipient of the inventive composition. At a minimum, it is often desirable that the donor and recipient are of the same species, though even xenogenic sources are permitted.

Once a bone sample is obtained, it is milled, ground, pulverized, or otherwise reduced to particulate form. In preferred embodiments, the particles will be greater than 75 microns in their minimum dimension, more preferably greater than 100 microns, and more preferably greater than 150 microns. In certain embodiments, the particles are at least 200 microns across the greatest dimension. The particles may be any shape including ovals, spherical, cuboidal, cones, pyramids, wedges, coils, coiled coils, etc. In certain embodiments, the particles are wedges, pyramids, or cones being 200 microns across their largest dimension. In other embodiments, the DBM composition may include a mixture of several different sizes and/or shapes of particles.

Following particulation, the DBM is treated to remove mineral from the bone. While hydrochloric acid is the industry-recognized demineralization agent of choice, the literature contains numerous reports of methods for preparing DBM (see, for example, Russell et al. *Orthopaedics* 22(5): 524-531, May 1999; incorporated herein by reference). For the purposes of the present invention, any material that provides a scaffold containing active osteoinductive factors is considered DBM. The DBM may be prepared by any methods known in the art or by other methods that can be developed by those of ordinary skill in the art without undue experimentation. In some instances, large fragments or even whole bone may be demineralized, and then particulated following demineralization. DBM prepared in this way is within the scope of the invention.

In preparing the improved DBM compositions, the DBM component may be ground or otherwise processed into particles of an appropriate size before or after demineralization. In certain embodiments, the particle size is greater than 75 microns, more preferably ranging from about 100 to about 3000 microns, and most preferably from about 200 to about 2000 microns. After grinding the DBM component to the desired size, the mixture may be sieved to select those particles of a desired size. In certain embodiments, the DBM particles may be sieved though a 50 micron sieve, more preferably a 75 micron sieve, and most preferably a 100 micron sieve.

One particularly useful way to limit the access of water to the DBM is to embed the DBM in a monolithic bioabsorbable matrix, and then fragment the particle-containing monolithic matrix into particle sizes greater than 70 microns, preferably greater than 100 microns, and most preferably greater than 150 microns in their smallest dimension. Preferred matrices for embedding small DBM particles include biocompatible polymers and setting calcium phosphate cements. Generally the particulate DBM/polymer weight ratio will range from about 1:5 to about 1:3. In the case of calcium phosphate, the DBM will be present from 25% up to 90% by weight, preferably from 50% to 80%, more preferably from 60% to 80%; and most preferably approximately 75%. Particulation of the monolith can be accomplished by conventional milling or grinding, or through the use of cryomilling, or freezing followed by pulverization. In one preferred embodiment, lyophilized or dehydrated DBM is embedded in a resorbable polymer. In a second preferred embodiment, lyophilized or dehydrated DBM is embedded in one of the setting calcium phosphates known to the art. Following particulation, the preparation may be further lyophilized and/or mixed with a carrier.

Strategies for Stabilizing Demineralized Bone Compositions

After the demineralized bone matrix has been prepared, any of the strategies described below may be used to stabilize the osteoinductive or osteoconductive activity of the DBM. The strategies include acidification, dehydration, use of water substitutes, use of protease inhibitors, and use of diffusion barriers. These strategies may be used alone or in combination. As would be appreciated by one of skill in this art, the strategy or strategies used to stabilize the DBM composition will depend on the use of the composition including the site of implantation, the time of course of osteoinductivity or osteoconductivity needed, handling requirements, the injury being repaired, etc.

Dehydration. Following preparation of DBM or an inventive DBM composition, the composition may be stored in its hydrated form or in a lyophilized or dehydrated form with the endogenous water removed. The osteoinductivity of the DBM composition has been shown to be unstable in hydrated form and has been shown to degrade rapidly at pH 7.4 at 37° C. (Urist et al. *J. Theor. Biol.* 38:155, 1973, incorporated herein by reference). Therefore, water may be removed from the matrix to improve its shelf-life. The lyophilized or dehydrated composition may have greater than 50%, greater than 60%, greater than 70%, greater than 80%, greater than 90%, greater than 95%, or greater than 98% of the water removed from the original sample. The water in the DBM may be removed in vacuo, for example, the DBM may be frozen and placed in a lyophilizer under reduced pressure to remove endogenous water until the desired level of dehydration is achieved. In other embodiments, the DBM is extracted with organic solvents such as diethyl ether, tetrahydrofaran (THF), ethyl acetate, butanol, etc., to remove water from the DBM. The extraction with organic solvent may be repeated to remove the desired amount of water from the matrix. The matrix may also be dehydrated by placing the matrix in a closed environment with a dessicant such as silica gel, DRI-RITE, $P_2O_5$, calcium carbonate, etc. In lyophilized or dehydrated form, the osteoinductive or osteoconductive activity of the inventive DBM composition is substantially more stable even when stored at room temperature or below over months to years. In certain preferred embodiments, the dehydrated or lyophilized DBM composition retains at least 99%, 95%, 90%, or 80% of its original activity after being stored at 37° C. for up to 1 week, up to 3 weeks, up to 5 weeks, up to 1 year, up to 2 years, or up to 3 years. In other embodiments, the lyophilized or dehydrated DBM composition retains at least 75%, 80%, 90%, 95%, 98%, or 99% of the biological activity of the original composition after 6 months, 1 year, or 2 years at room temperature or at 4° C. Preferably, the lyophilized or dehydrated DBM composition retains at least 90% of its original biological activity after 1 year at 4° C.

Acidification. Endogenous proteolytic enzymes have been implicated as the source of the instability of DBM at physiologic pH. (Urist et al. *J. Histochem. & Cytochem.* 22:88-103, 1974, incorporated herein by reference). The proteolytic activity of these endogenous protease can be reduced by lowering the pH of the DBM composition. At a pH between 2-6, preferably between 3-5, and more preferably between 3-4, the inventive DBM composition has an increased stability whether in a lyophilized or dehydrated form. In certain preferred embodiments, the acidified DBM composition retains at least 99%, 95%, 90%, or 80% of its original biological activity after being stored at 37° C. for up to 1 week, up to 3 weeks, up to 5 weeks, up to 1 year, up to 2 years, or up to 3 years. In other embodiments, the acidified and/or dehydrated DBM composition retains at least 75%, 80%, 85%, 90%, 95%, 98%, or 99% of the osteoinductive or osteoconductive activity of the original composition after 6 months, 1 year, or 2 years at room temperature or at 4° C.

In certain embodiments, the pH of the DBM composition is reduced below physiological pH (pH 7.4). The inventive DBM composition may be prepared by acidifying the DBM composition by rinsing and/or soaking the DBM in an acidic solution or buffered solution with the desired or lower pH, preferably <7, more preferably between approximately 2 and approximately 5, and most preferably between approximately 3 and approximately 4. hi certain embodiments, the DBM may be rinsed and/or soaked until the desired pH has been achieved. In other embodiments, the acidified DBM composition may be achieved by rinsing the demineralized DBM with water after the demineralization step, which is usually accomplished with an acid such as HCl. Rinsing with water or a buffered solution may continue after the demineralization step until the desired pH of the DBM has been achieved. The acidification step may occur before, during, or after the addition of additional stabilizing agents such diffusion barriers; protease inhibitors or other enzyme inhibitors; $D_2O$; covalent modifications chemicals; carriers; polyols, sorbitol; or water substitutes as described below.

As a result of the acidic environment of the DBM, the proteolytic activity of endogenous proteases is decreased resulting in increased stability of the osteoinductive factors present in the DBM. The increased stability of the acidified DBM compositions may be tested by any method known in the art including implanting the DBM composition intermuscularly in rats and looking for bone formation after a defined time period (see, Edwards et al. *Clinical Orthopaedics* 357:219-228, 1998, incorporated herein by reference). In a preferred embodiment, the osteoinductivity of a DBM composition retains >50%, >75%, >80%, >90%, >95%, or >98% of the original osteoinductivity of the DBM after 1 week, 3 weeks, 5 weeks, 6 months, 1 year, 1.5 years, 2 years, 3 years, and 10 years at 4° C., 25° C., room temperature, or 37° C.

The inventive acidified DBM composition with or without stabilizing agent added may be stored in hydrated or dehydrated/lyophilized form. The composition may contain from about 10% to about 99% water by weight. In certain preferred embodiments, the water content is >10% by weight. The composition may be stored at or below room temperature to further increase the self-life of the inventive DBM composition. As would be appreciated by one of skill in this art, decreasing the temperature will increase the half-life of the biological activity of the inventive DBM composition.

Deuterated water. Deuterated water has been shown to act as a stabilizing agent in biological compositions. For example, $D_2O$ has been shown to increase the stability of organic molecules, macromolecules, viruses, and vaccines (Katz, "The biology of heavy water" *Scientific American* July 1960, 106-115; Katz "Chemical and biological studies with deuterium" $39^{th}$ Priestly Lecture, Pennsylvania State University, 1-110; Jain et al. *Biochem. Biophys. Acta* 860:448, 1986; each of which is incorporated herein by reference). Crainic and Simpson have described increased thermal and microbial stability and slower disaggregation of certain macromolecules (published PCT application WO 94/21298; incorporated herein by reference). The presence of 95% $D_2O$ has been found to be equivalent to a 4-5° C. reduction in storage temperature compared to $H_2O$, for vaccines. hi addition, 7-25% $D_2O$ helps prevent protein denaturation (see Wenzel, DE2253086; Hamaya and Horikoshi, JP01179689; Teva Pharm. Industries, Ltd. EP 332826; each of which is incorporated herein by reference). The present invention demonstrates that the addition of deuterated water to DBM or the soaking or rinsing of DBM in deuterated water results in the stabilization of the osteoinductivity of DBM compositions. In certain embodiments, the DBM is dehydrated to remove $H_2O$ and then re-hydrated with $D_2O$. Preferably, the percentage of $D_2O$ is greater than 50%, more preferably greater than 75%, and even more preferably greater than 90%. In certain embodiments, the percentage of $D_2O$ is greater than 95%. However, in some embodiments, the percentage of $D_2O$ may be 5-10%, 10-20%, 20-30%, or 40-50%. In other embodiments, the pD of a $D_2O$ solution or buffer used to prepare a DBM compositions is below 7.0, preferably between 2 and 5, and more preferably between 3 and 4. By lowering the pD of the $D_2O$ solution or buffer, the osteoinductivity is further stabilized by reducing the activity of endogenous proteases as discussed above. The use of $D_2O$ as a water substitute may also be combined with other strategies for stabilizing DBM compositions such as adding a stabilizing agent such as a sugar, adding a protease inhibitor(s), and adding other water substitutes as described below.

Other water substitutes. Water substitutes may also inhibit chemical reactions in which water participates, or water is the required medium for the reaction. Water substitutes may include polyols such as glycerol, liquid polymers, flowable polymers, moldable polymers, polyethylene glycol, hydrogels, hyaluronic acid, liquid lipids, flowable lipids, moldable lipids, hydroxylated small molecules, DMSO, DMF, oils, emulsions of oil and water, emulsions of oil and degassed water, etc. Preferably, the water substitutes are biocompatible. Water substitutes inhibit chemical reactions in which water participates (e.g., isotope effects with $D_2O$) including enzymatic break-down of biologically active factors, and the thermodynamic destabilization of protein structure or is the required medium for the reaction. Therefore, even at room temperature the resulting DBM compositions with water substitutes have a greater shelf-life than DBM compositions without water substitutes. The effect of water substitutes may be further increased by storing the DBM compositions at lower temperatures. Other stabilizing agents and/or other methods of stabilizing DBM compositions (e.g., lowering pH) may also be used in conjunction with water substitutes.

Preferably the water substitute is liquid; however, semi-solid substances may also be used as water substitutes. In certain embodiments, the water substitutes include chemical compounds with hydroxyl groups or other polar functional groups such as amines, thiols, carbonyls, etc. In certain embodiments, the polar groups of the water substitute are capable of forming hydrogen bonds. The water substitute may be polar and freely miscible with water. In other embodiments, the water substitute is non-polar (e.g., an oil, lipid), and it may not be freely miscible with water. Examples of water substitutes include hydrogenated castor oil, bone marrow lipids, hydrogenated beef tallow, hydrogenated lard oil, cacao butter, polysaccharides, polyols, polyvinyl alcohol, polyethylene glycol, glycerol, fatty acid glycerol esters such as glycerol monolaurate, glycerol monomyristate, glycerol monopalmitate, glycerol monostearate, glycerol dilaurate, glycerol dimyristate, glycerol dipalmitate, glycerol distearate, glycerol trimyristate, glycerol tripalmitate, and glycerol tristearate. In certain embodiments, the DBM composition does not include glycerol.

Examples of waxy materials that may be used as water substitutes include beeswax, carnauba wax, Japan wax, spermaceti, hydrocarbons such as paraffin, micro-crystalline wax, and fatty alcohols such as cetyl alcohol, and stearyl alcohol as well as higher fatty acids such as lauric acid, myristic acid, palmitic acid, stearic acid, behenic acid, and arachidic acid.

The addition of water substitutes to a composition also has the benefit of making the composition flowable and moldable.

Addition of stabilizing agents. The incorporation of stabilizing agents into the inventive formulations is generally accomplished by suspending the molecule or molecules of interest in an appropriately compatible buffer as will be known to those skilled in the art. This buffer is then mixed with matrix in a relatively low liquid-to-solid volume ratio to form a slurry. Preferably, the pH of the buffer is approximately pH 7.4. In embodiments where the composition is acidified, the pH of the buffer is less than physiological pH is approximately the pH desired in the final DBM composition. In certain embodiments, the buffer with the stabilizing agent(s) is mixed with lyophilized matrix. The slurry may then be lyophilized and used to prepare the desired DBM formulations.

One feature of the instant invention is that the incorporation of diffusion barriers, enzyme inhibitors (e.g., protease inhibitors), competitive substrates, masking agents, or other stabilizing agents often has the additional feature of further improving the DBM formulation's shelf-life by preventing access of endogenously present degradative enzymes to the active factors present in the matrix. This is particularly true for DBM formulations which are prepared containing water (e.g., DBM preparations with hydrogel carriers such as hyaluronic acid or collagen, or hydrated starch carriers).

Diffusion barriers retard the diffusion of degradative enzymes and/or water to the active moieties within the inventive formulations. Enzymes retarded in their diffusion to the included DBM may be capable of releasing the active factor from the matrix, and/or degrading or inactivating the active factor. They also may act by retarding diffusion of the active factors from the implant site. In these ways, the barriers provide for longer residence time of the active factors at the implant site. This is particularly useful for forming bone in higher species such as humans, where bone formation appears to require the presence of active factors for longer times.

Generally, materials most suitable to serve as diffusion barriers will be easily mixed with DBM or synthetic matrix of choice to form a gel, paste, or putty-like consistency, although in some embodiments, the barrier/matrix formulation will be prepared as a relatively non-deformable solid (e.g., for matrix preparations to be used in posterior lateral spine fusion). In preferred embodiments, the diffusion barriers themselves degrade in a predictable manner to unmask active factors at a time later than would normally occur in the absence of a diffusion barrier. Resorbable polymers with known hydrolytic rates are useful as diffusion barriers as well as enzymatically degraded polymers. Particularly useful are lipase susceptible lipid based carriers such as fatty acids and phospholipids, which mix well with DBM. In certain DBM embodiments, the composition does not include phosphatidylcholine. Some particularly effective preparations provide prolonged stability by controlled unmasking of the osteoinductive factors. These preparations generally involve the use of two or more diffusion barriers with different degradation times affording at least two different rates of unmasking the same active factor.

Biodegradable polymers useful in preparing inventive stabilized matrix/growth factor compositions include natural polymers such as proteins (e.g., collagen) and polysaccharides (e.g., starch, modified starch, maltrin) as well as man-made resorbable polymers such as poly-orthoesters. These polymers when mixed with the inventive growth factor containing compositions retard diffusion of the host's degradative enzymes and/or water to the active factors contained within the composition, thereby retarding release and/or degrading of the active factor contained therein.

Polymers that may be included within inventive compositions include, for example, natural polymers such as lipids, polysaccharides, proteoglycans, and proteins. Preferred polysaccharides include starches, dextrans, and celluloses, and preferred proteins include collagen. Polysaccharides such as starches, dextrans, and celluloses may be unmodified or may be modified physically or chemically to affect one or more of their properties such as their characteristics in the hydrated state, their solubility, their susceptibility to degradation, or their half-life in vivo. Polysaccharides such as starches and celluloses are attractive as they also have known degradation rates. Generally, the celluloses degrade more slowly within the body, breaking down on the order of weeks or months, while many starch and lipid preparations degrade rapidly, on the order of hours or days. Starch in the natural state is a mixture of two polysaccharides, amylose and amylopectin. The susceptibility of the particular starch to the starch-degrading enzymes such as amylase, pectinases, and β-glucosidase is an important consideration in designing the inventive formulations. Those skilled in the art are aware of the variety of amylase susceptibilities of starches prepared from various plant sources and may apply this knowledge to produce formulations having a desired stability time. Preferred starches will degrade as much as 10% per day, preferably 50% per day, and most preferably greater than 90% per day. Those starches less susceptible to degradation by pectinase and/or amylase (amylase-resistant starch; Starch Australasia, Sydney, Australia) may be used to maximally extend the osteoinductive half-life in vivo to an even greater extent than improved DBM or synthetic growth factor/matrix formulations prepared from more enzyme susceptible starches. Some modified starches are less susceptible to degradation by amylase; therefore, improved DBM with modified starch would presumably have a longer half-life in vivo as compared to those improved DBM with unmodified starch. One preferred method to affect amylase susceptibility of starch is through the use of starch lipid combinations. Guidance for the combination of lipid and starch to affect amylase susceptibility is given by Crowe et al "Inhibition of Enzymic Digestion of Amylose by Free Fatty Acids In Vitro Contributes to Resistant Starch Formation" *J. Nutr.* 130(8):2006-2008, August 2000; incorporated herein by reference. Similar considerations apply to lipids and their degradative enzymes the lipases. A large variety of mono-, di-, and triglycerides with varying degrees of susceptibility to lipase degradation are available from commercial sources. Some embodiments include one or more polymeric materials, preferably biodegradable, such as tyrosine polycarbonates, polyfumarates, tyrosine polyarylates, and poly-orthoesters such as polylactide, polygalactide, and co-polymers thereof. These polymers are biodegradable, and their properties can be modified by altering the chain length or degree of cross-linking of the polymer and/or the chemical structure of the monomers. Additionally, co-polymers can be prepared using combinations of resorbable polymers.

Enzyme inhibitors useful in the practice of the present invention may include, for example, acid protease inhibitors, serine protease inhibitors, metalloprotease inhibitors (see Whittaker et al. "Matrix Metalloproteinases and their Inhibitors—Current Status and Future Challenges" *Celltranssmissions* 17(1):3-14; incorporated herein by reference), cysteine protease inhibitors, glyconase inhibitors, and glycosidase inhibitors. Specific protease inhibitors useful in the practice of the present invention include, for example, aprotinin, 4-(2-aminoethyl)benzenesulfonyl fluoride (AEBSF), amastatin-HCl, alpha1-antichymotrypsin, antithrombin II, alpha1-antitrypsin, 4-aminophenylmethane sulfonyl-fluoride (APMSF), arphamenine A, arphamenine B, E-64, bestatin, CA-074, CA-074-Me, calpain inhibitor I, calpain inhibitor II, cathepsin inhibitor, chymostatin, diisopropylfluorophosphate (DFP), dipeptidylpeptidase IV inhibitor, diprotin A, E-64c, E-64d, E-64, ebelactone A, ebelactone B, EGTA, elastatinal, foroxymithine, hirudin, leuhistin, leupeptin, alpha2-macroglobulin, phenylmethylsulfonyl fluoride (PMSF), pepstatin A, phebestin, 1,10-phenanthroline, phosphoramidon, chymostatin, benzamidine HCl, antipain, epsilon-aminocaproic acid, N-ethylmaleimide, trypsin inhibitor, 1-chloro-3-tosylamido-7-amino-2-heptanone (TLCK), 1-chloro-3-tosylamido-4-phenyl-2-butanone (TPCK), trypsin inhibitor, sodium EDTA, and the TIMPs class of metalloproteinase inhibitors. Particularly useful ones are those stable under acidic conditions and effective at acidic conditions.

Use of competitive substrates for the host's degradative or activating enzymes may also be employed to stabilize the osteoinductive factors of the DBM or exogenously added growth factors. Examples of competitive substrates include di- and poly-lysines. Di- and polysaccharides can be employed as competitive substrates of glycosidases, amylases, and/or pectinases. Particularly useful are stereoisomers of the competitive substrates.

Specific masking entities are generally used to specifically block a single entity or class of entities from enzymatic breakdown. The degradative or activating enzyme to be blocked may be endogenous or exogenous to the matrix. The masking entities generally bind to a ligand present on the matrix which may or may not be the active factor itself. Once bound the masking entity sterically hinders the breakdown and/or release of one or more active factors. Over time the masking entity either unbinds or itself is degraded leaving the ligand and or growth factor susceptible to degradation. Diffusion barriers represent a generalized form of masking entity by preventing access of the degradative or activating enzymes to many or all the growth factors associated with the matrix.

Covalent Modification of DBM. The DBM may be covalently modified by the addition of polyethylene glycol or silylation.

Exemplary stabilized DBM compositions. Based on the above strategies for stabilizing DBM compositions and those discussed in other applications which are incorporated herein by reference, the following DBM compositions are particularly useful:

Certain DBM compositions do not include glycerol. In certain embodiments, the DBM composition comprises DBM and a non-glycerol stabilizing means. The stabilizing means may include a water substitute such as deuterated water, polyols, lipids, oils, waxes, polysaccharides, etc.; protease inhibitors; acids; diffusion barriers; competitive substrates; masking agents; and covalent modifications. In certain particular embodiments, the stabilizing means is a water substitute, protease inhibitor, acid, or a diffusion barrier. Particularly useful water substitutes are $D_2O$ and non-glycerol polyols. In certain embodiments, the DBM composition is acidified, and a water substitute is added. In other embodiments, the DBM compositions is acidified and a protease inhibitor is added. In yet other embodiments, the DBM composition includes a water substitute and a protease inhibitor. Water from the DBM composition may optionally be removed by lyophilization or other means as described herein. The DBM composition should preferably retain at least 95% of its original osteoinductive activity after 1 year at room temperature.

The inventive DBM composition may further comprise a non-glycerol carrier. Non-glycerol carriers useful in the include DBM compositions include hyaluronic acid, collagen, lipid, polymers, and water. A carrier may be added to the DBM composition to make the composition more flowable, easier to mold, and/or easier to work with. Preferably, the addition of a carrier does not substantially affect the stability or half-life of the DBM composition.

In certain embodiments, the DBM composition include glycerol as a water substitute. In certain embodiments, the DBM composition includes DBM, glycerol, and stabilizing means. The stabilizing means may be a water substitute, acidification, diffusion barrier, or protease inhibitor. Examples of particularly useful stabilizing means include hyaluronic acid, starch, and lipid.

In certain embodiments, the DBM is mixed with an exogenous destabilizing entity. For example, the DBM may be mixed with a tissue containing proteases or other degradatory enzymes. In order to protect the active factors in the DBM from degradation, the various strategies outlined above may be used to stabilize the otherwise destabilized composition. For example, a protease inhibitor may be added to the composition in order to at least partially counteract the effect of the exogenous destabilizing entity.

Test for Stabilization

The invention also provides an in vitro test for the screening of suitable stabilizing agents. DBM compositions prepared as described herein are exposed under simulated physiological conditions (e.g., pH 7.4, physiological saline) to an enzyme or combination of enzymes known to be capable of degrading some or all of the protein constituents of the DBM. Most often this will be a protease such as trypsin, pepsin, papain, peptidase, or the like. Evidence for matrix or matrix component breakdown is compared between the two preparations. Materials retarding the breakdown process are considered to be good candidates for further testing. Preferred indicators of breakdown include immunological detection of TGF-β and/or IGF breakdown. In addition to the enzymes indicated above, other enzymes such as collagenases or combinations of enzymes as well as glycosidases may also be used. Particularly useful in this regard is the natural degradatory activity of serum or tissue extracts. Under these conditions, specific marker proteins present in the DBM may be tracked by immunological methods such as radioimmunoassay or gel electrophoresis utilizing western blots, or other analytical methods known in the art. For example, the degradation of particular proteins may be monitored, or the increase in level of degradatory products such as peptide fragments may be monitored.

Following the identification of candidate stabilizers in the above assay, the DBM formulations containing the candidate stabilizers are tested in the osteoinductivity assays described elsewhere herein.

Accelerated Stability Testing

The invention also provides an in vitro test for accelerated stability testing. Several replicate samples of each DBM formulation are packaged in moisture resistant containers (aluminum foil) and placed at elevated temperatures (e.g., 40° C.) for a period of several months. At various times (e.g., 0, 5.3, 10.6, 21.2, and 31.8 weeks post-incubation), the packages are opened and the osteoinductive activity of the contents is determined. The accelerated stability of any sample can be determined from the slope of the best fit line obtained by plotting the osteoinductive activity of each DBM formulation, normalized to percent initial osteoinductive activity, against time. The room temperature stability of the materials could be extrapolated using Von't Hoff' s rule of enzyme kinetics as described by Reick et al., *Medical Device and Diagnostic Industry* 10(3):34-39, 1998; incorporated herein by reference.

In our studies as shown below in the Examples, acidifying the DBM composition or adding glycerol to a hydrated a DBM formulation, significantly increases the osteoinductive stability of DBM.

Measurement of Osteoinductive Activity

Osteoinductive activity is determined by implanting the DBM formulation of interest in a nonskeletal site in an athymic rat and evaluating the amount of new bone, cartilage, and bone marrow that is induced at the site of the implant. The procedure for determination of osteoinductive activity has previously been described in detail (Edwards J T, Diegmann M H, Scarborough N L. "Osteoinduction of human demineralized bone: characterization in a rat model" *Clin. Orthop.* 1998 December; (357):219-28; incorporated herein by reference).

Osteoinducer

To the DBM composition may be added other osteoinducing agents. These agents may be added in an activated or non-activated form. These agents may be added at anytime during the preparation of the inventive material. For example, the osteoinducing agent may be added after the demineralization step and prior to the addition of the stabilizing agents so that the added osteoinducing agent is protected from exogenous degrading enzymes once implanted. In some embodiments the DBM is lyophilized in a solution containing the osteoinducing agent. In certain other preferred embodiments, the osteoinducing agents are adhered onto the hydrated demineralized bone matrix and are not freely soluble. In other instances, the osteoinducing agent is added to the improved DBM after addition of the stabilizing agent so that the osteoinducing agent is available immediately upon implantation of the DBM.

Osteoinducing agents include any agent that leads to or enhances the formation of bone. The osteoinducing agent may do this in any manner, for example, the agent may lead to the recruitment of cells responsible for bone formation, the agent may lead to the secretion of matrix which may subsequently undergo mineralization, the agent may lead to the decreased resorption of bone, etc. Particularly preferred osteoinducing agents include bone morphogenic proteins (BMPs), transforming growth factor (TGF-$\beta$), insulin-like growth factor (IGF-1), hormones including parathyroid hormone (PTH), and angiogenic factors such as VEGF. In one preferred embodiment (Example 12), the inducing agent is genetically engineered to comprise an amino acid sequence which promotes the binding of the inducing agent to the DBM or the carrier. Sebald et al. in PCT/EP00/00637, incorporated herein by reference, describe the production of exemplary engineered growth factors, suitable for use with DBM.

Formulation

Improved osteogenic compositions of the present invention may be formulated for a particular use. The formulation may be used to alter the physical, biological, or chemical properties of a DBM preparation. A physician would readily be able to determine the formulation needed for a particular application taking into account such factors as the type of injury, the site of injury, the patient's health, the risk of infection, etc.

Inventive compositions therefore may be prepared to have selected resorption/loss of osteoinductivity rates, or even to have different rates in different portions of an implant. For example, the formulation process may include the selection of DBM particles of a particular size or composition, combined with the selection of a particular stabilizing agent or agents, and the amounts of such agents. To give but one example, it may be desirable to provide a composition whose osteoinductive factors are active in a relatively constant amount over a given period of time. A DBM composition comprising factors with longer half-lives can be prepared using a less biodegradable polymer or a larger amount (e.g., a thicker coating) of polymeric compound. The amount or type of protease inhibitor may also be adjusted to provide a DBM composition with a desired half-life. Alternatively or additionally, the particle size may be important in determining the half-life of the inventive DBM composition. In certain preferred embodiments, an inventive formulation may include a mixture of particles, each with a different half-life. Such a mixture could provide the steady or possible unmasking of osteoinductive factors over an extended period of time ranging from days to weeks to months depending on the needs of the injury. Compositions such as this can be formulated to stimulate bone growth in a human patient comparable to the bone growth induced by treatment with 10 $\mu$g of rhBMP on a collagen sponge, and preferably comparable to 100 $\mu$g, and most preferably 1-10 mg rhBMP.

Physical properties such as deformability and viscosity of the DBM may also be chosen depending on the particular clinical application. The particles of the improved DBM may be mixed with other materials and factors to improve other characteristics of the implant. For example, the improved DBM material may be mixed with other agents to improve wound healing. These agents may include drugs, proteins, peptides, polynucleotides, solvents, chemical compounds, biological molecules, etc.

The particles of DBM (or inventive DBM material) may also be formed into various shapes and configurations. The particles can be formed into rods, strings, sheets, weaves, solids, cones, discs, fibers, wedges, coils, coiled coils, etc. In certain embodiments, the shape and size of the particles in the DBM composition affect the time course of osteoinductivity. For example, in a cone or wedge shape, the tapered end will result in osteoinductivity shortly after implantation of the DBM composition, whereas the thicker end will lead to osteoinductivity later in the healing process (e.g. hours to days to weeks later). Il certain embodiments, the particle have a length of greater than 2 mm, greater than 1.5 mm, greater than 1 mm, preferably greater than 500 microns, and most preferably greater than 200 microns across its widest dimension. Also, larger particle size will have induced bone formation over a longer time course than smaller particles. Particles of different characteristics (e.g., composition, size, shape) may be used in the formation of these different shapes and configurations. For example, in a sheet of DBM a layer of long half-life particles may be alternated between layers of shorter half-life particles (see U.S. Pat. No. 5,899,939, incorporated herein by reference). In a weave, strands composed of short half-life particles may be woven together with strands of longer half-lives.

In one preferred embodiment of the invention, fibrous DBM is shaped into a matrix form as described in U.S. Pat. No. 5,507,813, incorporated herein by reference. The shaped DBM is then embedded within a diffusion barrier type matrix, such that a portion of the matrix is left exposed free of the matrix material. Particularly preferred blocking matrices are starch, phosphatidyl choline, tyrosine polycarbonates, tyrosine polyarylates, polylactides, polygalactides, or other resorbable polymers or copolymers. Devices prepared in this way from these matrices have a combination of immediate and longer lasting osteoinductive properties and are particularly useful in promoting bone mass formation in human posterolateral spine fusion indications.

In another embodiment of the invention, inventive DBM compositions having a pre-selected three-dimensional shape are prepared by repeated application of individual layers of DBM, for example by 3-D printing as described by Cima et al. U.S. Pat. Nos. 5,490,962; and 5,518,680, each of which is incorporated herein by reference; and Sachs et al. U.S. Pat. No. 5,807,437, incorporated herein by reference. Different layers may comprise individual stabilized DBM preparations, or alternatively may comprise DBM layers treated with stabilizing agents after deposition of multiple layers.

In the process of preparing improved inventive DBM materials, the materials may be produced entirely aseptically or be sterilized to eliminate any infectious agents such as HIV, hepatitis B, or hepatitis C. The sterilization may be accomplished using any method or combination of methods, including one or more of antibiotics, irradiation, chemical sterilization (e.g., ethylene oxide), or thermal sterilization. Other methods known in the art of preparing DBM such as defatting, sonication, and lyophilization may also be used in preparing the improved DBM. Since the biological activity of demineralized bone is known to be detrimentally affected by most terminal sterilization processes, care must be taken when sterilizing the inventive compositions. In preferred embodiments, the DBM compositions described herein will be prepared aseptically or sterilized as described in Example 6.

Applications

Improved osteogenic compositions of the present invention may be used to promote the healing of bone injuries. The compositions may be used in any bone of the body on any type of injury. The improved DBM composition has been designed to produce bone in human patients with similar timing and at a level similar to 10 µg to 100 µg, preferably 200 µg to 1 mg of rhBMP on a collagen sponge. For example, specific bones that can be repaired using the inventive material include the ethmoid, frontal, nasal, occipital, parietal, temporal, mandible, maxilla, zygomatic, incus, stapes, malleus, cervical vertebrae, thoracic vertebrae, lumbar vertebrae, sacrum, sternum, ribs, clavicle, scapula, humerus, ulna, radius, carpal bones, metacarpal bones, phalanges, ileum, ischium, pubis, pelvis, femur, patella, tibia, fibula, calcaneus, talus, and metatarsal bones. The type of injury amenable to treatment with the improved DBM include bone defects resulting from injury, brought about during the course of surgery, infection, malignancy, or developmental malformation. The inventive material may be useful in orthopaedic, neurosurgical, cosmetic, and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery (e.g., deficit filling), discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc.

These and other aspects of the present invention will be further appreciated upon consideration of the following Examples, which are intended to illustrate certain particular embodiments of the invention but are not intended to limit its scope, as defined by the claims.

EXAMPLES

Example 1

Preparing Demineralized Bone Matrix (DBM)

DBM may be prepared using any method or technique known in the art (see Russell et al. *Orthopedics* 22(5):524-531, May 1999; incorporated herein by reference). The following is an exemplary procedure for preparing demineralized bone derived from Glowacki et al. "Demineralized Bone Implants" *Clinics in Plastic Surgery* 12(2):233-241, April 1985, which is incorporated herein by reference. Bones or bone fragments from donors are cleaned to remove any adherent periosteum, muscle, connective tissue, tendons, ligaments, and cartilage. Cancellous bone may be separated from dense cortical bone and processed as large pieces. Cortical bone may be cut into small pieces to improve the efficiency of subsequent washes and extractions. Denser bone from larger animals may need to be frozen and hammered in order to produce chips less than 1 cm. The resulting pieces of bone are thoroughly washed with cold, deionized water to remove marrow and soft tissue.

The cleaned bone is then extracted with frequent changes of absolute ethanol for at least 1 hour. Typically, a total of 4 liters of ethanol is used per 100 g of bone. The bone is then extracted with frequent changes of anhydrous diethyl ether in a fume hood for 1 hour. Typically, 2 liters of ether is used per 100 g of bone. The bone is dehydrated by these extractions of ethanol and ether and can be stored at room temperature.

The dehydrated bone is then frozen and then pulverized in a liquid nitrogen impacting mill. Pulverized bone is then sieved into fractions of 75 to 250, 250 to 450, and greater than 450 microns. Bone particle fractions are then demineralized using 0.5 M hydrochloric acid (50 ml per gram) for 3 hours at room temperature or at 4° C. on magnetic stirrers with insulation to prevent overheating. Large chips of bone and blocks are extracted completely at 4° C. with frequent changes of 0.5 M hydrochloric acid. The demineralization process can be monitored radiographically, by ashing, or by nondecalcified histologic techniques (von Kossa stain). The acid and liberated minerals are washed away with cold, deionized water until the pH of the wash matches the pH of the water. The water washes can be decanted from the large particles and chips of bone; however, the washes must be removed by centrifugation from the finer particles. The washing step requires approximately 500 ml of water per gram of starting bone particles.

Demineralized bone powders are extracted with changes of absolute ethanol for 1 hour using 200 ml of ethanol per gram of starting bone particles. The material is extracted in a fume hood with changes of anhydrous ethyl ether for 1 hour with 100 ml of ether per gram of starting bone particles. After the last change of ether is removed, the demineralized bone powder is left overnight in the hood until all the residual ether has vaporized. The particles should be odorless, snow-white, and discrete. To sterilize the demineralized bone material, it may be treated with cold ethylene oxide or irradiated.

To test the bioactivity of the prepared DBM, 25 mg of the material is implanted into each of two thoracic subcutaneous pockets in shaved, anesthetized 28-day old male Charles River CD rats. The implanted specimens may then be harvested and inspected several days after implantation. The composition of the induced tissue can be quantified by histomorphometric analysis and biochemical techniques.

Example 2

Another Method of Preparing DBM.

DBM may be prepared using any method or techniques known in the art (See Russell et al *Orthopedics* 22(5):524-531, May 1999; incorporated herein by reference).

Demineralized bone matrix was prepared from long bones. The diaphyseal region was cleaned of any adhering soft tissue and then ground in a mill. Ground material was sieved to yield a powder with particles approximately 100 µm to 500 µm in diameter. The particulate bone was demineralized to less than about 1% (by weight) residual calcium using a solution of Triton X-100 (Sigma Chemical Company, St Louis, Mo.) and 0.6N HCl at room temperature followed by a solution of fresh 0.6N HCl. The powder material was rinsed with deionized water until the pH was greater than 3.0. It then was soaked in 70% ethanol and freeze-dried to less than 5% residual moisture.

Example 3

In Vitro Assessment of pH-stabilized DBM

Samples of pH stabilized DBM with or without stabilizing agents (or various concentrations and/or formulations of stabilizing agents) are prepared and incubated with serum or individual enzymes (e.g., papain) in PBS buffer (pH 7.4) and incubated at 37° C. for 0.5, 1, 2, 4, 8, and 24 hours Samples are then extracted to determine the concentrations of growth factors and other matrix proteins as outlined in Ueland et. al. ("Increased cortical bone content of insulin-like growth factors in acromegalic patients" *J. Clin. Endocrinol. Metab.* 1999 January; 84(1):123-7; incorporated herein by reference). Samples are prepared for native and denaturing SDS gel electrophoresis followed by Western blot analysis or Western Ligand blotting as described in Ueland et al. (1999) and incorporated herein by reference (Ueland et al "Increased cortical bone content of insulin-like growth factors in acromegalic patients" *J Clin Endocrinol Metab* 1999 January; 84(1):123-7; and Walker, J. M. (Ed) *The Protein Protocols Handbook*, Second Edition 2002, Humana Press Totowa, New Jersey; each of which is incorporated herein by reference).

Samples may then be tested for osteoinductivity at 7, 14, 21, 28, 30, 60, or 90 days in the athymic rat assay or other appropriate species. Extract samples can also be tested rapidly for biological activity in a tissue culture assay as described in Zhang et al. (1997).

Example 4

Determining Time Course for Induction of Bone Growth by Intermuscular Implant

This Example characterizes the time course of induction of bone growth in an intermuscular site using the inventive materials, as compared with DBM base powder (as in Example 1), at time points of 7, 14, 28, and 35 days. This Example is similar to the rat model for assessing osteoinduction of DBM found in Edwards et al. "Osteoinduction of Human Demineralized Bone: Characterization in a Rat Model" *Clinical Orthopaedics* 357:219-228, December 1998; incorporated herein by reference.

The study is conducted in athymic (nude) rats in order to minimize the potential for a cross-species incompatibility response to human tissue implants. The hind-limb intermuscular site is used for the initial determination of heterotopic bone induction properties because the site does not naturally contain bone.

Female homozygous mu/mu rats in the 50-75 g range are obtained from Harlan (Indianapolis, Ind.). The rats are housed for one week for acclimatization purposes prior to surgery. Sterile microisolator cages are used throughout the investigation, with sterile water and rodent diet provided ad libitum.

Implant Placement: A single intermuscular (IM) site is utilized in each hind limb of 30 rats. To provide a common positive control over all animals, a single 40 mg sample of rat DBM powder is placed intramuscularly within the left pectoralis (LP) muscle of each rat. Animals are allowed normal activities following surgical procedures.

Implant Materials: DBM and test materials are kept at room temperature. Samples are tested for implantation times of 7, 14, and 28 days. Samples of DBM powder are rehydrated with 100 Ill of sterile ALLOPREP™ (Ostetotech, Eatontown, N.J.). Each of the samples is packed into a 1 ml blunt cut syringe. Implantation is randomized so that a single animal does not receive two of the same implants.

Anesthesia: The rats are anesthetized with a mixture of ketamine (200 mg), xylazine (400 mg), and physiological saline (10 ml). The dosage is 3.5 ml/kg body weight administered intraperitoneally.

Procedure: Aseptic surgical procedures are carried out in a laminar airflow hood. A 1-cm skin incision is made on each upper hind limb using a lateral approach, and the skin is separated from the muscle by blunt dissection. A superficial incision aligned with the muscle plane is made to allow for insertion of the tips of the scissors. Blunt dissection is performed from this line deep into the muscle to create a pocket to hold the implanted material. A single suture is inserted to close the muscle pocket, and the skin is closed with metal clips.

Implantation of specimens in the left pectoralis muscles involves making a 1-cm skin incision over the chest, blunt dissection of the muscle to create a pocket, and positioning of the rat DBM powder using a blunt syringe. A single suture is inserted to close the muscle pocket, and the skin is closed with metal clips.

Rats are euthanized with $CO_2$ following the designated implantation time. Implant materials are located by palpitation, retrieved by blunt dissection, and cleaned of the surrounding tissue by careful trimming. An observer blinded to implant type performed a macroscopic evaluation of the implant material. Color, vascularity, hardness, and integrity are scored according to the scheme outlined in the Table below. (The highest score for the most robust response would be a 4 while a specimen showing little or no osteoinductive potential would score a 0.) Experience with this model has shown a high correlation between visual observations and histological observations of implant performance only at the extremes of both ends of the scale.

| Macroscopic Observation Scoring Guidelines | | | |
|---|---|---|---|
| Color: | White (W) | Grey (G) | Red (R) |
| Vascularity: | None (N) | Some (S) | Robust (R) |
| Hardness: | Mushy (M) | Firm (F) | Hard (H) |
| Integrity: | Diffuse (D) | Flat (F) | Nodule (N) |
| Score: | 0 | 0.5 | 1 |

Histology: Retrieved materials are fixed in Neutral buffered formalin. After fixation in formalin, samples are decalcified in 10% formic acid, dehydrated in graded alcohols, embedded in JB-4 (glycol methacrylate, Polysciences, Inc., Warrington, Pa.) and sectioned. Five-micron sections are stained with toluidine blue and evaluated by light microscopy.

These explants are histologically evaluated using a semi-quantitative method. Briefly, a numerical score based on a five-point scale is assigned to each section of nodule: 4=more than 75% involved in new bone formation; 3=51-75% involved in new bone formation; 2=26-50% involved in new bone formation; 1=1-25% of the explant involved in new bone formation; and 0=no evidence for the process of endochondral bone formation including the presence of cartilage or chondrocytes, active osteoblasts, osteoid, newly formed and mineralized bone, and/or marrow and associated fat cells.

| Scoring of Histological Sections | |
|---|---|
| Score | New Bone Formation |
| 0 | No new bone formation |
| 1 | <25% new bone formation |
| 2 | 26-50% new bone formation |
| 3 | 51-75% new bone formation |
| 4 | >75% new bone formation |

Following histological analysis, average scores are calculated for each material type. Based on previous experience with this animal model, each group is assigned an assessment of osteoinductive, potential based on the average histological score.

Example 5

Osteoinduction in a Rabbit Model

Fifty-five male New Zealand White rabbits are assigned to three treatment groups. Test article was prepared as described herein. Those animals assigned to the Low Dose treatment group (n=20) receive 3.5 ml of the test article in the right paravertebral muscle following a protocol specified procedure. Animals assigned to the High Dose treatment group (n=20) receive 3.5 ml of the test article in the right paravertebral muscle and 7.0 ml of the test article in the subcutaneous tissue of each side of the dorsal thoracic area. The animals assigned to the Control treatment group (n=15) are implanted with 3.5 ml of control article (rehydrated DBM powder) in the right paravertebral muscle. At 7, 14, and 28 days post-implantation, four animals from the Low and High Dose treatment groups and three animals from the Control groups are humanely sacrificed. At 60 days post-implantation, the remaining animals are sacrificed (eight from the Low and High Dose test groups and six from the Control treatment group). The implant sites are collected from each rabbit and fixed in 10% neutral buffered formalin (NBF). The test and control implant sites from the 60 days post-implantation study interval are placed in decalcification solutions for 3 days after adequate formalin fixation. All tissue samples are processed using standard histological techniques, sectioned at 5 µm, and stained with hematoxylin and eosin.

Example 6

Terminal Sterilization

This example describes a terminal sterilization method which minimizes osteoinductivity loss in the inventive preparations.

The inventive DBM preparations are produced in a clean room environment from human tissue. The finished implants are placed in individual tray packages.

Each tray is placed in an Audionvac sealing apparatus (Audion Electro B.V., Weesp-Holland) which is supplied with a cylinder consisting of 50/50 hydrogen/argon gas. Before the tray packages are sealed, they are evacuated and backfilled with the gas mixture twice. Following sealing, the gas mixture remains in each tray package.

The packaged implants are then sealed packages and then treated with 15 KGy gamma radiation from a cobalt 60 source to reduce the bioburden of the implants to the desired level.

Example 7

Storage of Acidic DBM at Room Temperature

To determine the stability of acidic DBM in real time, a DBM composition comprising pooled human demineralized bone powder (100-500 micron particle size) at pH ~5.0 was prepared and subjected to storage at room temperature. Sixteen samples were prepared for each time point and half of the DBM samples were then stored in hydrated form, while endogenous water was removed by lyophilization from the second half. Test samples were packed in foil pouches, sealed and stored at ambient temperature and humidity for 0, 5.3, 10.6, 21.3, and 31.8 weeks until implantation. Samples were implanted inter-muscularly in the upper thigh of female nude rats as described in Edwards et al. *Clinical Orthopaedics* 357:219-228, 1998; incorporated herein by reference. The DBM was subsequently explanted 28 days after surgery for histological evaluation and scoring of osteoinductivity as described in the above reference. Results of histological studies showed that there was no significant decrease in the osteoinductivity of DBM samples which were stored hydrated or lyophilized for up to 31.8 weeks (FIG. 7). These data indicate that an acidic DBM is stable at room temperature in either hydrated or lyophilized form for at least 31.8 weeks.

|  | 0 weeks | 5.3 weeks | 10.6 weeks | 21.2 weeks | 31.8 weeks |
|---|---|---|---|---|---|
| Hydrated DBM | 4 | 3.5 | 4 | 3.5 | 3.5 |
| Lyophilized DBM | 4 | 3.5 | 3.5 | 3.5 | 3.5 |

Example 8

Storage of Acidic DBM at 40° C.

To evaluate the long term stability of acidic DBM, a DBM composition comprising pooled human demineralized bone powder (100-500 micron particle size) at pH 5.0 was prepared and subjected to accelerated aging. Sixteen samples were prepared for each time point. Half of the DBM samples were then stored in hydrated form, and the other half were stored in lyophilized form by removing endogenous water. Test samples were packed in foil pouches, sealed, and stored at 40° C.±2° C., 75%±5% relative humidity, for 0, 5.3, 10.6, 21.2, and 31.8 weeks until implanted. Applying the Arrhenius reaction rate equation which states that a 10° C. increase in temperature results in approximately a two times change in the rate of a chemical reaction (Q10=2) storage at 40° C. for the times indicated can be equivalent to room temperature, real time storage up to three years. Samples were implanted inter-muscularly in the upper thigh of female nude rats as described in Edwards et al. *Clinical Orthopaedics* 357:219-228, 1998, incorporated herein by reference. The DBM was subsequently explanted 28 days after surgery for histological evaluation and scoring of osteoinductivity of DBM samples which were stored lyophilized for up to an equivalent of 3 years (based on accelerated aging). In contrast, DBM samples which were stored in the hydrated form lost about 50% of their osteoinductivity in the same time frame (based on accelerated aging) (FIG. 8). These data indicate that while both storage method, i.e., hydrated or lyophilized retain the osteoinductivity of the acidic DBM, a lyophilized acidic DBM is more stable and retains at least 75% of its osteoinductivity up to three years.

|  | Real Time Equivalent | | | | |
|---|---|---|---|---|---|
|  | 0 weeks | 6 months | 12 months | 24 months | 36 months |
| Hydrated DBM | 4 | 3.25 | 2 | 2 | 1.5 |
| Lyophilized DBM | 4 | 3.25 | 3.2 | 2.75 | 3 |

Example 9

Storage of Acidic DBM plus Starch Carrier at 40° C.

To assess the stability of an acidic DBM containing a starch carrier, a DBM comprising pooled human demineralized bone powder (100-500 micron particle size) and a carrier (maltodextrin, modified starch, and water) at pH ~4.3 was made and subjected to accelerated aging at 40° C. Samples were packaged and sealed in foil packages. Accelerated aging testing was done at 40° C.±2° C., 75%±5% relative humidity. Eight samples were prepared for each time point and stored in hydrated form. Samples were packed in foil pouches, sealed and stored at 40° C.±2° C., 75%±5% relative humidity, for 0, 5.3, 10.6, 21.2, and 31.8 weeks until implanted. Storage at 40° C. for the times indicated is equivalent to room temperature, real time storage up to 0, 6, 12, 24, and 36 months, respectively (based on $Q_{10}$=2). Each accelerated-aging sample had a real time sample analyzed in parallel after 0, 6, 12, 24, and 36 months of aging at room temperature. Samples were implanted inter-muscularly in the upper thigh of female nude rats as described in Edwards et al. *Clinical Orthopaedics* 357:219-228, 1998, incorporated herein by reference. The DBM was subsequently explanted 28 days after surgery for histological evaluation and scoring of osteoinductivity as described in the above reference. Results of histological studies showed that there was only a slight difference between samples tested under real time and the real time equivalent of accelerated aging conditions. These data indicate that an acidic DBM containing a starch carrier retains more than 75% and about 80% of its osteoinductivity after three years. This also demonstrates that there is a correlation between real time aging of DBM and accelerated aging.

|  | 0 weeks | 6 months | 12 months | 24 months | 36 months |
|---|---|---|---|---|---|
| Real time DBM | 3.5 | 3.2 | 3.0 | — | — |
| Accelerated DBM | 3.5 | 3.2 | 3.3 | 3.1 | 2.8 |

Example 10

Storage of Acidic versus Neutral DBM at 40° C.

To compare the long term stability of an acidic pH DBM to a neutral pH DBM, a DBM comprising pooled human demineralized bone powder (100-500 micron particle size) is made, pH adjusted, and subjected to accelerated aging. Accelerated aging testing is done at 40° C.±2° C., 75%±5% relative humidity. Samples at each pH are prepared for each time point and stored in hydrated form. Test samples are packed in foil pouches, sealed, and stored at 40° C.±2° C., 75%±5% relative humidity, for 0, 5.3, 10.6, 21.2, and 31.8 weeks until implanted. Storage at 40° C. for the times indicated is equivalent to room temperature, real time storage of as much as 0, 6, 12, 24, and 36 months, respectively ($Q_{10}$=2). Samples are implanted inter-muscularly in the upper thigh of female nude rats as described in Edwards et al. *Clinical Orthopaedics* 357:219-228, 1998, incorporated herein by reference. The DBM is subsequently explanted 28 days after surgery for histological evaluation and scoring of osteoinductivity as described in the above reference. Results of histological studies should indicate acidic DBM maintains osteoinductive stability for at least 3 years while the osteoinductivity of pH neutral DBM is less stable.

Example 11

Stabilization of a Neutral DBM with a Hyaluronic Acid Carrier

To evaluate the stability of a neutral DBM which has been pH stabilized with a hyaluronic acid carrier, a neutral pH DBM comprising pooled human demineralized bone powder (100-500 micron particle size) is made with and without a hyaluronic acid carrier and subjected to accelerated aging.

Eight samples are prepared with and without a hyaluronic acid carrier for each time point and stored in hydrated form. Test samples are packed in foil pouches, sealed, and stored at 40° C.±2° C., 75%±5% relative humidity, for 0, 2, and 5.3 weeks until implanted. Applying the Arrhenius equation, storage at 40° C. for 5.3 weeks is equivalent to up to approximately one year real time storage. Samples are implanted inter-muscularly in the upper thigh of female nude rats as described in Edwards et al. *Clinical Orthopaedics* 357:219-228, 1998, incorporated herein by reference. The DBM is subsequently explanted 28 days after surgery for histological evaluation and scoring of osteoinductivity as described in the above reference. Results of histological studies are expected to show that the addition of a hyaluronic acid carrier to a pH neutral DBM maintains osteoinductive stability for at least 1 year or more while the osteoinductivity of pH neutral DBM is less stable.

Figure 3:
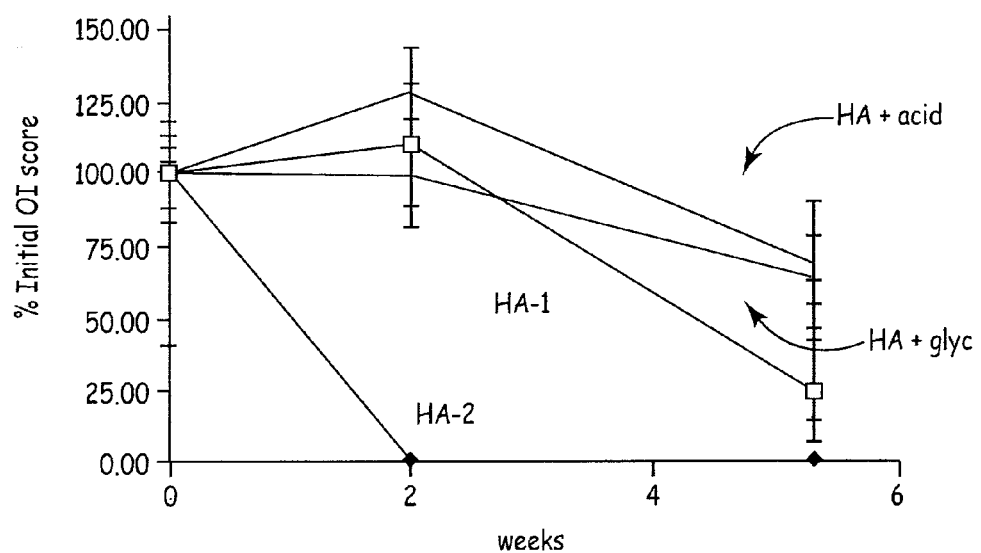
FIG. 3. After 5 weeks at accelerated temperatures, both non-stabilized hyaluronic acid containing samples had less than 50% of their starting osteoinductivity. The two stabilized samples had greater than 50% of their starting activity. Regression analysis were performed for all samples. The slopes (degradation rates) determined from these analysis are presented in table in Example 11. Slopes for DBM, lyophilized or in the presence of water determined in previous studies are included in the table for comparison purposes.

Results: After 5 weeks at accelerated temperatures, both non-stabilized hyaluronic acid containing samples had less than 50% of their starting osteoinductivity (see FIG. 3). The two stabilized samples had greater than 50% of their starting activity. Regression analysis were performed for all samples. The slopes (degradation rates) determined from these analysis are presented in the table below. Slopes for DBM, lyophilized or in the presence of water determined in previous studies, are included in the table for comparison purposes.

| Degradation Rates of Various Demineralized Bone Preparations at 40° C. | |
| --- | --- |
| Preparation | Degradation rate (% OI/week) |
| Lyophilized DBM | 0.36-0.52 |
| Lyophillized DBM plus glycerol | 0.58 |
| DBM hydrated with water (pH < 5) | 1.4 |
| HA + glycerol | 6.7 |
| HA + acid | 7.2 |
| HA-1 | 15.3 |
| HA-2 | 16.9 |

Example 12

Stabilization of a Neutral DBM with a Collagen Carrier

To evaluate the stability of a neutral DBM composition which has been pH stabilized with the addition of a collagen carrier, a neutral pH DBM comprising pooled human demineralized bone powder (100-500 micron particle size) is made with and without a collagen carrier and subjected to accelerated aging. Accelerated aging testing is done at 40° C.±2° C., 75%±5% relative humidity. Samples are prepared with and without a collagen carrier for each time point and stored in hydrated form. Test samples are packed in foil pouches, sealed, and stored at 40° C.±2° C., 75%±5% relative humidity, for 0, 5.3, 10.6, 21.2, and 31.8 weeks until implanted. Storage at 40° C. for the times indicated is equivalent to room temperature, real time storage up to 0, 6, 12, 24, and 36 months, respectively ($Q_{10}=2$). Samples are implanted inter-muscularly in the upper thigh of female nude rats as described in Edwards et al. *Clinical Orthopaedics* 357:219-228, 1998, incorporated herein by reference. The DBM is subsequently explanted 28 days after surgery for histological evaluation and scoring of osteoinductivity as described in the above reference. Results of histological studies should indicate that the addition of a collagen carrier to a pH neutral DBM maintains osteoinductive stability for at least 3 years or more while the osteoinductivity of pH neutral DBM is less stable.

Example 13

Preparation of DBM Stabilized with Lipid

A known amount of lecithin is solubilized in a known volume of 70% or 100% ethanol. For example, 4.5 g, 2.25 g, or 1.125 g of lecithin is dissolved in 13.5 ml of ethanol. The resulting mixture of lecithin in ethanol may optionally be filtered through a 0.2 micron filter. The lecithin/alcohol mixture is then added to DBM (4.5 g), and the material is allowed to penetrate the matrix for 30 minutes. The material is then frozen and lyophilized. The lecithin-DBM composition can then be used in formulating bone replacement materials. The lipid-stabilized DBM may offer benefits including improved look and feel, enhanced activity, improved stability, and increased shelf life.

Example 14

DBM Formulations

Preparation of DBM Formulations. DBM formulations are prepared as described in the table below. Hydrophobic lipids are added to the DBM in an appropriate solvent (acetone, chloroform, etc.), and the material is lyophilized prior to addition of hydrated carriers. Where tissues are treated with irreversible protease inhibitors, the protease inhibitors would generally be washed out prior to implantation of tissue. Starch should be cooked (autoclaved in the presence of water) prior to mixing with DBM.

| Bone Forming Agent | Carrier | Stabilizing Means |
| --- | --- | --- |
| 20 g DBM | 10 g Hyaluronic acid | 100 cc 1% Glycerol |
| 20 g DBM | 10 g Hyaluronic acid | 100 cc 10% Glycerol |
| 20 g DBM | 10 g Hyaluronic acid | 100 cc 20% Glycerol |
| 20 g DBM | 10 g Hyaluronic acid | 100 cc 30% Glycerol |
| 20 g DBM | 10 g Hyaluronic acid | 100 cc 40% Glycerol |
| 20 g DBM | 10 g Hyaluronic acid | 100 cc 50% Glycerol |
| 20 g DBM | 10 g Hyaluronic acid | 100 cc 60% Glycerol |
| 20 g DBM | 10 g Hyaluronic acid | 100 cc 70% Glycerol |
| 20 g DBM | 10 g Hyaluronic acid | 100 cc 80% Glycerol |
| 20 g DBM | 10 g Hyaluronic acid | 100 cc 90% Glycerol |
| 20 g DBM | 10 g Hyaluronic acid | 100 cc 99% Glycerol |
| 20 g DBM | 10 g B-980 Starch | 60 cc 40% Dimethysulfoxide |
| 20 g DBM | 10 g B-980 Starch | 60 cc 1.5 M Glycine |
| 20 g DBM | 10 g B-980 Starch | 60 cc 2.5 M Proline |
| 20 g DBM | 10 g B-980 Starch | 60 cc 1.2 M Sucrose |
| 20 g DBM | 10 g B-980 Starch | 60 cc 1.0 M Trehalose |
| 20 g DBM | 10 g B-980 Starch | 60 cc 200 mM $K_2PO_4$ |
| 20 g DBM | 10 grams Hydrated Carrier (starch, etc.) | 5 grams hydrophobic lipid (tripalmitate, cholesterol, etc) |
| 20 g DBM | 10 g Hyaluronic acid | 60 cc 40% Dimethysulfoxide |
| 20 g DBM | 10 g Hyaluronic acid | 60 cc 1.5 M Glycine |
| 20 g DBM | 10 g Hyaluronic acid | 60 cc 2.5 M Proline |
| 20 g DBM | 10 g Hyaluronic acid | 60 cc 1.2 M Sucrose |
| 20 g DBM | 10 g Hyaluronic acid | 60 cc 1.0 M Trehalose |
| 20 g DBM | 10 g Hyaluronic acid | 60 cc 200 mM $K_2PO_4$ |
| 20 g DBM | 10 g Hyaluronic acid | 5 grams hydrophobic lipid (tripalmitate, cholesterol, etc.) |

-continued

| Bone Forming Agent | Carrier | Stabilizing Means |
|---|---|---|
| 20 g DBM | 10 grams non DBM protease containing tissue (mineralized bone, etc.) | 100 cc (1-99%) Glycerol |
| 20 g DBM | 10 grams non DBM protease containing tissue (mineralized bone | 20 g hydrophobic lipid (tripalmitate, cholesterol, etc.) |
| 20 g DBM | 10 grams non DBM protease containing tissue (mineralized bone | 60 cc 2 mM N-ethylmaleimide |
| 20 g DBM | 10 grams non DBM protease containing tissue (mineralized bone | 60 cc 0.1 mM 4-(2-Aminoethyl)benzenesulfonyl-fluoride HCl |
| 20 g DBM | 10 grams hydrated non DBM protease containing tissue (mineralized bone | Heat treatment at 59° C. for 2 hrs |

Stability testing. Samples are packaged in moisture resistant containers (aluminum foil) and placed at room temperature for a period of time exceeding 3 years. At various time periods (e.g., 1 month, 3 months, 6 months, 1 year, 2 years, 3 years, 4 years, 5 years, etc.), the packages are opened, and the osteoinductivity of the sample is measured in an appropriate animal model (e.g., athymic rat). The osteoinductive stability of any sample could be determined from the slope of the line obtained by plotting osteoinductive activity of the sample against time. Accelerated stability studies may be carried out at elevated temperatures (e.g., 37° C. or 45° C.), and the results extrapolated to room temperature stability.

Measurement of Osteoinductive Activity. Osteoinductive activity is determined by implanting the DBM formulation of interest in a nonskeletal site in an athymic rat and evaluating the amount of new bone, cartilage, and bone marrow that is induced at the site of the implant. The procedure for determination of osteoinductive activity has previously been described in detail (Edwards J T, Diegmann M H, Scarborough N L. "Osteoinduction of human demineralized bone: characterization in a rat model" *Clin. Orthop.* 1998 December, (357):219-28; incorporated herein by reference).

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

The invention claimed is:
1. A demineralized bone matrix composition comprising:
demineralized bone matrix; and
at least one non-glycercol stabilizing means;
wherein the composition retains at least 50% of its original osteoinductivity after one year at room temperature, and
wherein the non-glycerol stabilizing means is a non-glycerol polyol selected from the group consisting of polynivyl alcohols and polyethylene glycols.
2. The composition of claim 1, wherein the composition does not include glycerol.
3. The composition of claim 1, wherein the demineralized bone matrix is in the form selected from the group consisting fibers, plates, particles, threads, and gels.
4. The composition of claim 1 further comprising water.
5. The composition of claim 1 further comprising hyaluronic acid.
6. The composition of claim 1, wherein the non-glyercol stabilizing means is a protease inhibitor or combination of protease inhibitors.
7. The composition of claim 6, wherein the protease inhibitor is selected from the group consisting of aprotinin, 4-(2-aminoethyl)benzenesulfonyl fluoride (AEBSF), amastatin-HCl, alpha1-antichymotrypsin, antithrombin III, alpha1-antitrypsin, 4-aminophenylmethane sulfonyl-fluoride (APMSF), arphamenine A, arphamenine B, E-64, bestatin, CA-074, CA-074-Me, calpain inhibitor I, calpain inhibitor II, cathepsin inhibitor, chymostatin, diisopropylfluorophosphate (DFP), dipeptidylpeptidase IV inhibitor, diprotin A, E-64c, E-64d, E-64, ebelactone A, ebelactone B, EGTA, elastatinal, foroxymithine, hirudin, leuhistin, leupeptin, alpha2-macroglobulin, phenylmethylsulfonyl fluoride (PMSF), pepstatin A, phebestin, 1,10-phenanthroline, phosphoramidon, chymostatin, benzamidine HCl, antipain, epsilon-aminocaproic acid, N-ethylmaleimide, trypsin inhibitor, 1-chloro-3-tosylamido-7-amino-2-heptanone (TLCK), 1-chloro-3-tosylamido-4-phenyl-2-butanone (TPCK), trypsin inhibitor, sodium EDTA, and combinations thereof.
8. The composition of claim 1, wherein the pH of the composition is below 7.
9. The composition of claim 1, wherein the pH of the composition is below 5.
10. The composition of claim 1, wherein the pH of the composition is below 4.
11. The composition of claim 1, wherein the pH of the composition is below 2.
12. The composition of claim 1, wherein the pH of the composition is between approximately 3 and 4.
13. The composition of claim 1, wherein the pH of the composition is between approximately 4 and 5.
14. The composition of claim 1, wherein the composition retains at least 75% of its original osteoinductivity after 1 year at room temperature.
15. The composition of claim 1, wherein the composition retains at least 90% of its original osteoinductivity after 1 year at room temperature.
16. The composition of claim 1, wherein the composition retains at least 75% of its original osteoinductivity after 2 years at room temperature.
17. The composition of claim 1, wherein the composition retains at least 90% of its original osteoinductivity after 2 years at room temperature.
18. The composition of claim 1 further comprising at least one exogenous osteoinductive or osteogenic agent.
19. The composition of claim 1 further comprising:
a non-glycerol carrier.
20. The composition of claim 19, wherein the carrier is selected from the group consisting of hyaluronic acid, collagens, lipids, polymers, proteins, and water.
21. The composition of claim 19, wherein the carrier is selected from the group consisting of hyaluronic acid, collagens, lipids, polymers, and water.
22. The composition of claim 19, wherein the carrier is selected from the group consisting of deuterated water (D$_2$O), protease inhibitors, non-glycerol polyols, sorbitol, and acids.
23. A demineralized bone matrix composition comprising:
an exogenous destabilizing agent.
24. The composition of claim 23, wherein the exogenous destabilizing agent is a protease.
25. The composition of claim 23, wherein the exogenous destabilizing agent is a tissue comprising a protease.

* * * * *